(12) United States Patent
Matringe et al.

(10) Patent No.: US 7,279,302 B2
(45) Date of Patent: Oct. 9, 2007

(54) METHODS FOR IDENTIFYING HERBICIDAL COMPOUNDS

(75) Inventors: Michel Matringe, Lyons (FR); Pascal Rippert, Lyons (FR)

(73) Assignee: Bayer CropScience S.A. (FR)

( * ) Notice: Subject to any disclaimer, the term of this patent is extended or adjusted under 35 U.S.C. 154(b) by 399 days.

(21) Appl. No.: 10/433,556

(22) PCT Filed: Dec. 5, 2001

(86) PCT No.: PCT/FR01/03832

§ 371 (c)(1),
(2), (4) Date: Dec. 18, 2003

(87) PCT Pub. No.: WO02/46441

PCT Pub. Date: Jun. 13, 2002

(65) Prior Publication Data

US 2004/0117872 A1    Jun. 17, 2004

(30) Foreign Application Priority Data

Dec. 5, 2000 (FR) .................................. 00 15723

(51) Int. Cl.
*C12Q 1/32* (2006.01)

(52) U.S. Cl. ........................ 435/26; 435/69.2; 435/190

(58) Field of Classification Search ................... 435/26, 435/69.2, 190
See application file for complete search history.

(56) References Cited

U.S. PATENT DOCUMENTS 5,187,071 A * 2/1993 Fischer et al. ................ 435/32

* cited by examiner

*Primary Examiner*—Ralph Gitomer
(74) *Attorney, Agent, or Firm*—Connolly Bove Lodge & Hutz LLP

(57) ABSTRACT

The invention concerns novel enzymes having an arogenate dehydrogenase activity, in particular arogenate dehydrogenase enzymes of plants, and the genes encoding said enzymes. The inventive arogenate dehydrogenase enzymes catalyze the last stage of the metabolic pathway of tyrosine biosynthesis, and constitute, as such, potential targets of herbicides. Hence the invention also concerns a method for identifying herbicide compounds targeting said enzymes, said herbicide compounds preventing tyrosine biosynthesis by being fixed on said enzymes. The invention further concerns transgenic plants tolerant to herbicide compounds targeting an enzyme involved in the tyrosine biosynthesis pathway, in particular an enzyme involved in the transformation of L-tyrosine prephenate, in particular an arogenate dehydrogenase enzyme. Said plants become tolerant by expression in their tissues of a prephenate dehydrogenase enzyme, said enzyme being insensitive to said herbicide compounds and enabling the plant to synthetize tyrosine despite being treated with said herbicide compounds.

2 Claims, 4 Drawing Sheets

| Plasmid overexpressed | $K_m$ NADP (µM) | $K_m$ arogenate (µM) | $K_i$ tyrosine (µM) | Native molecular weight (Da) |
|---|---|---|---|---|
| pET 21 TyrA-ATc | 40 ± 5.6 | 70 ± 16 | 14 ± 2 | 65 000 |
| pET 21 TyrA-AT1 | 75 ± 2 | 45 ± 9.2 | 8 ± 1 | 124 000 |
| pET 21 TyrA-AT2 | 20 ± 2.5 | 45 ± 5.6 | 12 ± 2 | 69 000 |

Figure 3

| | $V_{max}$ (µmol/min/mg protein) | $K_m$ NADP (µM) | $K_m$ arogenate (µM) |
|---|---|---|---|
| pure TyrA sy | 88,1 | 6 | 107 |

Figure 4

SEQUENCE LISTING

```
<160> NUMBER OF SEQ ID NOS: 30

<210> SEQ ID NO 1
<211> LENGTH: 2082
<212> TYPE: DNA
<213> ORGANISM: Arabidopsis thaliana
<220> FEATURE:
<221> NAME/KEY: transit_peptide
<222> LOCATION: (1)..(174)
<220> FEATURE:
<221> NAME/KEY: Intron
```

<222> LOCATION: (1089)..(1181)

<400> SEQUENCE: 1

| | | | | | |
|---|---|---|---|---|---|
| atgatctttc | aatctcattc | tcatcatctt | cttctctatc | aatcctcatc | ttcctcctcc | 60 |
| ttcttcttcc | tcccaaagct | catcaccaaa | cctcctctct | ccctctcatt | tacctctctt | 120 |
| tcctcaatgc | tcccttctct | ctctctctcc | accgccaacc | gccacctctc | cgtcaccgac | 180 |
| accatccctc | ttcccaactc | caactccaac | gccaccccte | ctctccgtat | cgccatcatc | 240 |
| ggattcggaa | actacggcca | attccttgcc | gaaaccctaa | tttctcaagg | ccacattctc | 300 |
| ttcgctcact | cccgatccga | tcactcctcc | gccgctcgcc | gtctcggtgt | ctcatacttc | 360 |
| accgatcttc | acgatctctg | cgaacgtcat | cctgacgtag | tccttctctg | tacttcaatc | 420 |
| ctctccatag | agaatattct | caaaacgttg | ccgtttcaga | gactccgtcg | caacactctc | 480 |
| ttcgttgatg | ttctctccgt | taaagagttt | gctaaaactc | ttctccttca | atacttacct | 540 |
| gaagatttcg | atattctttg | tacacatcca | atgtttggtc | ctcagagtgt | gagttcaaat | 600 |
| catggctgga | gaggattaag | atttgtgtat | gataaagtta | ggattgggga | agagagattg | 660 |
| agagtctcaa | ggtgtgagag | tttttcttgag | attttttgtta | gagaaggatg | tgagatggtg | 720 |
| gagatgagtg | ttactgatca | tgataagttt | gctgctgaat | cacagtttat | aactcatact | 780 |
| cttggtaggc | ttttggggat | gttgaagttg | atatcgacgc | cgattaatac | gaaagggtac | 840 |
| gaggcgttgc | ttgatttagc | tgagaatatt | tgtggggata | gttttgattt | gtattatggg | 900 |
| ttgtttgtgt | ataataacaa | ctctttggag | gtgttagaga | ggattgattt | ggctttcgag | 960 |
| gctttgcgta | aggagctttt | tagtcggctt | cacggtgttg | tgaggaagca | gtcttttgaa | 1020 |
| ggtgaagcaa | agaaagttca | tgtttttcca | aattgtggtg | aaaatgatgc | ttcttttggat | 1080 |
| atgatgaggt | atgtagttag | ttagttagtt | acattgtgtg | gtttgatgca | ttttggattt | 1140 |
| ggtttcttat | tgtaaatagt | tatcgatttg | tgatcttgca | ggtcagaaga | tgttgttgtg | 1200 |
| aagtatgaat | ataactccca | ggtgtctggt | agtgttaatg | acggttcgag | gctcaagatt | 1260 |
| ggtatcgtcg | ggtttggaaa | ttttggacag | tttctaggta | aaaccatggt | caagcagggt | 1320 |
| cacactgtgt | tagcttattc | cagaagtgac | tacactgatg | aagcagcaaa | gctcggtgtt | 1380 |
| tcgtattttt | cagatcttga | tgatctattt | gaagagcatc | ctgaagttat | tattctctgt | 1440 |
| acgtcaatcc | tttcgactga | aaaagttctc | gagtcactac | cgtttcagag | actgaagaga | 1500 |
| agcacacttt | ttgtggatgt | actctcagta | aaagagttcc | cgaggaattt | atttcttcaa | 1560 |
| actctcccac | aagattttga | tattttgtgc | acgcatccta | tgtttgggcc | agagagtggt | 1620 |
| aaaaatggat | ggaacaatct | tgcctttgtg | tttgataagg | ttaggattgg | aatggatgat | 1680 |
| agaagaaaat | cgaggtgtaa | cagttttctt | gatatttttg | cccgtgaagg | atgtcgtatg | 1740 |
| gtggagatgt | cgtgtgctga | acatgattgg | catgctgctg | gatcacagtt | tatcacacac | 1800 |
| acagtgggaa | ggcttctgga | gaagctgagc | ttggaatcta | ctcctataga | taccaaaggt | 1860 |
| tatgagacat | tgctaaaact | ggtggagaat | actgctggtg | acagctttga | tctgtactat | 1920 |
| ggactatttt | tatacaatcc | taatgcaatg | gaacagcttg | agaggtttca | tgtggctttt | 1980 |
| gaatcattga | agacacagct | ctttggacga | ctacattctc | aacattctca | tgagctagct | 2040 |
| aaatcatctt | ccccaaagac | aactaagcta | ttaactagct | aa | | 2082 |

<210> SEQ ID NO 2
<211> LENGTH: 1981
<212> TYPE: DNA
<213> ORGANISM: Arabidopsis thaliana

```
<220> FEATURE:
<221> NAME/KEY: CDS
<222> LOCATION: (1)..(1980)
<220> FEATURE:
<221> NAME/KEY: transit_peptide
<222> LOCATION: (1)..(174)

<400> SEQUENCE: 2 atg atc ttt caa tct cat tct cat cat ctt ctt ctc tat caa tcc tca        48
Met Ile Phe Gln Ser His Ser His His Leu Leu Leu Tyr Gln Ser Ser
1               5                   10                  15 tct tcc tcc tcc ttc ttc ttc ctc cca aag ctc atc acc aaa cct cct        96
Ser Ser Ser Ser Phe Phe Phe Leu Pro Lys Leu Ile Thr Lys Pro Pro
                20                  25                  30 ctc tcc ctc tca ttt acc tct ctt tcc tca atg ctc cct tct ctc tct       144
Leu Ser Leu Ser Phe Thr Ser Leu Ser Ser Met Leu Pro Ser Leu Ser
            35                  40                  45 ctc tcc acc gcc aac cgc cac ctc tcc gtc acc gac acc atc cct ctt       192
Leu Ser Thr Ala Asn Arg His Leu Ser Val Thr Asp Thr Ile Pro Leu
        50                  55                  60 ccc aac tcc aac tcc aac gcc acc cct cct ctc cgt atc gcc atc atc       240
Pro Asn Ser Asn Ser Asn Ala Thr Pro Pro Leu Arg Ile Ala Ile Ile
65                  70                  75                  80 gga ttc gga aac tac ggc caa ttc ctt gcc gaa acc cta att tct caa       288
Gly Phe Gly Asn Tyr Gly Gln Phe Leu Ala Glu Thr Leu Ile Ser Gln
                85                  90                  95 ggc cac att ctc ttc gct cac tcc cga tcc gat cac tcc tcc gcc gct       336
Gly His Ile Leu Phe Ala His Ser Arg Ser Asp His Ser Ser Ala Ala
            100                 105                 110 cgc cgt ctc ggt gtc tca tac ttc acc gat ctt cac gat ctc tgc gaa       384
Arg Arg Leu Gly Val Ser Tyr Phe Thr Asp Leu His Asp Leu Cys Glu
        115                 120                 125 cgt cat cct gac gta gtc ctt ctc tgt act tca atc ctc tcc ata gag       432
Arg His Pro Asp Val Val Leu Leu Cys Thr Ser Ile Leu Ser Ile Glu
    130                 135                 140 aat att ctc aaa acg ttg ccg ttt cag aga ctc cgt cgc aac act ctc       480
Asn Ile Leu Lys Thr Leu Pro Phe Gln Arg Leu Arg Arg Asn Thr Leu
145                 150                 155                 160 ttc gtt gat gtt ctc tcc gtt aaa gag ttt gct aaa act ctt ctc ctt       528
Phe Val Asp Val Leu Ser Val Lys Glu Phe Ala Lys Thr Leu Leu Leu
                165                 170                 175 caa tac tta cct gaa gat ttc gat att ctt tgt aca cat cca atg ttt       576
Gln Tyr Leu Pro Glu Asp Phe Asp Ile Leu Cys Thr His Pro Met Phe
            180                 185                 190 ggt cct cag agt gtg agt tca aat cat ggc tgg aga gga tta aga ttt       624
Gly Pro Gln Ser Val Ser Ser Asn His Gly Trp Arg Gly Leu Arg Phe
        195                 200                 205 gtg tat gat aaa gtt agg att ggg gaa gag aga ttg aga gtc tca agg       672
Val Tyr Asp Lys Val Arg Ile Gly Glu Glu Arg Leu Arg Val Ser Arg
    210                 215                 220 tgt gag agt ttt ctt gag att ttt gtt aga gaa gga tgt gag atg gtg       720
Cys Glu Ser Phe Leu Glu Ile Phe Val Arg Glu Gly Cys Glu Met Val
225                 230                 235                 240 gag atg agt gtt act gat cat gat aag ttt gct gct gaa tca cag ttt       768
Glu Met Ser Val Thr Asp His Asp Lys Phe Ala Ala Glu Ser Gln Phe
                245                 250                 255 ata act cat act ctt ggt agg ctt ttg ggg atg ttg aag ttg ata tcg       816
Ile Thr His Thr Leu Gly Arg Leu Leu Gly Met Leu Lys Leu Ile Ser
            260                 265                 270 acg ccg att aat acg aaa ggg tac gag gcg ttg ctt gat tta gct gag       864
Thr Pro Ile Asn Thr Lys Gly Tyr Glu Ala Leu Leu Asp Leu Ala Glu
```

-continued

```
                275                 280                 285
aat att tgt ggg gat agt ttt gat ttg tat tat ggg ttg ttt gtg tat    912
Asn Ile Cys Gly Asp Ser Phe Asp Leu Tyr Tyr Gly Leu Phe Val Tyr
    290                 295                 300 aat aac aac tct ttg gag gtg tta gag agg att gat ttg gct ttc gag    960
Asn Asn Asn Ser Leu Glu Val Leu Glu Arg Ile Asp Leu Ala Phe Glu
305                 310                 315                 320 gct ttg cgt aag gag ctt ttt agt cgg ctt cac ggt gtt gtg agg aag   1008
Ala Leu Arg Lys Glu Leu Phe Ser Arg Leu His Gly Val Val Arg Lys
                325                 330                 335 cag tct ttt gaa ggt gaa gca aag aaa gtt cat gtt ttt cca aat tgt   1056
Gln Ser Phe Glu Gly Glu Ala Lys Lys Val His Val Phe Pro Asn Cys
            340                 345                 350 ggt gaa aat gat gct tct ttg gat atg atg agg tca gaa gat gtt gtt   1104
Gly Glu Asn Asp Ala Ser Leu Asp Met Met Arg Ser Glu Asp Val Val
        355                 360                 365 gtg aag tat gaa tat aac tcc cag gtg tct ggt agt gtt aat gac ggt   1152
Val Lys Tyr Glu Tyr Asn Ser Gln Val Ser Gly Ser Val Asn Asp Gly
    370                 375                 380 tcg agg ctc aag att ggt atc gtc ggg ttt gga aat ttt gga cag ttt   1200
Ser Arg Leu Lys Ile Gly Ile Val Gly Phe Gly Asn Phe Gly Gln Phe
385                 390                 395                 400 cta ggt aaa acc atg gtc aag cag ggt cac act gtg tta gct tat tcc   1248
Leu Gly Lys Thr Met Val Lys Gln Gly His Thr Val Leu Ala Tyr Ser
                405                 410                 415 aga agt gac tac act gat gaa gca gca aag ctc ggt gtt tcg tat ttt   1296
Arg Ser Asp Tyr Thr Asp Glu Ala Ala Lys Leu Gly Val Ser Tyr Phe
            420                 425                 430 tca gat ctt gat gat cta ttt gaa gag cat cct gaa gtt att att ctc   1344
Ser Asp Leu Asp Asp Leu Phe Glu Glu His Pro Glu Val Ile Ile Leu
        435                 440                 445 tgt acg tca atc ctt tcg act gaa aaa gtt ctc gag tca cta ccg ttt   1392
Cys Thr Ser Ile Leu Ser Thr Glu Lys Val Leu Glu Ser Leu Pro Phe
    450                 455                 460 cag aga ctg aag aga agc aca ctt ttt gtg gat gta ctc tca gta aaa   1440
Gln Arg Leu Lys Arg Ser Thr Leu Phe Val Asp Val Leu Ser Val Lys
465                 470                 475                 480 gag ttc ccg agg aat tta ttt ctt caa act ctc cca caa gat ttt gat   1488
Glu Phe Pro Arg Asn Leu Phe Leu Gln Thr Leu Pro Gln Asp Phe Asp
                485                 490                 495 att ttg tgc acg cat cct atg ttt ggg cca gag agt ggt aaa aat gga   1536
Ile Leu Cys Thr His Pro Met Phe Gly Pro Glu Ser Gly Lys Asn Gly
            500                 505                 510 tgg aac aat ctt gcc ttt gtg ttt gat aag gtt agg att gga atg gat   1584
Trp Asn Asn Leu Ala Phe Val Phe Asp Lys Val Arg Ile Gly Met Asp
        515                 520                 525 gat aga aga aaa tcg agg tgt aac agt ttt ctt gat att ttt gcc cgt   1632
Asp Arg Arg Lys Ser Arg Cys Asn Ser Phe Leu Asp Ile Phe Ala Arg
    530                 535                 540 gaa gga tgt cgt atg gtg gag atg tcg tgt gct gaa cat gat tgg cat   1680
Glu Gly Cys Arg Met Val Glu Met Ser Cys Ala Glu His Asp Trp His
545                 550                 555                 560 gct gct gga tca cag ttt atc aca cac aca gtg gga agg ctt ctg gag   1728
Ala Ala Gly Ser Gln Phe Ile Thr His Thr Val Gly Arg Leu Leu Glu
                565                 570                 575 aag ctg agc ttg gaa tct act cct ata gat acc aaa ggt tat gag aca   1776
Lys Leu Ser Leu Glu Ser Thr Pro Ile Asp Thr Lys Gly Tyr Glu Thr
            580                 585                 590 ttg cta aaa ctg gtg gag aat act gct ggt gac agc ttt gat ctg tac   1824
```

```
Leu Leu Lys Leu Val Glu Asn Thr Ala Gly Asp Ser Phe Asp Leu Tyr
        595                 600                 605 tat gga cta ttt tta tac aat cct aat gca atg gaa cag ctt gag agg    1872
Tyr Gly Leu Phe Leu Tyr Asn Pro Asn Ala Met Glu Gln Leu Glu Arg
    610                 615                 620 ttt cat gtg gct ttt gaa tca ttg aag aca cag ctc ttt gga cga cta    1920
Phe His Val Ala Phe Glu Ser Leu Lys Thr Gln Leu Phe Gly Arg Leu
625                 630                 635                 640 cat tct caa cat tct cat gag cta gct aaa tca tct tcc cca aag aca    1968
His Ser Gln His Ser His Glu Leu Ala Lys Ser Ser Ser Pro Lys Thr
                645                 650                 655 act aag cta tta a                                                  1981
Thr Lys Leu Leu
        660

<210> SEQ ID NO 3
<211> LENGTH: 660
<212> TYPE: PRT
<213> ORGANISM: Arabidopsis thaliana

<400> SEQUENCE: 3

Met Ile Phe Gln Ser His Ser His His Leu Leu Leu Tyr Gln Ser Ser
1               5                   10                  15

Ser Ser Ser Ser Phe Phe Phe Leu Pro Lys Leu Ile Thr Lys Pro Pro
            20                  25                  30

Leu Ser Leu Ser Phe Thr Ser Leu Ser Ser Met Leu Pro Ser Leu Ser
        35                  40                  45

Leu Ser Thr Ala Asn Arg His Leu Ser Val Thr Asp Thr Ile Pro Leu
    50                  55                  60

Pro Asn Ser Asn Ser Asn Ala Thr Pro Pro Leu Arg Ile Ala Ile Ile
65                  70                  75                  80

Gly Phe Gly Asn Tyr Gly Gln Phe Leu Ala Glu Thr Leu Ile Ser Gln
                85                  90                  95

Gly His Ile Leu Phe Ala His Ser Arg Ser Asp His Ser Ser Ala Ala
            100                 105                 110

Arg Arg Leu Gly Val Ser Tyr Phe Thr Asp Leu His Asp Leu Cys Glu
        115                 120                 125

Arg His Pro Asp Val Val Leu Leu Cys Thr Ser Ile Leu Ser Ile Glu
    130                 135                 140

Asn Ile Leu Lys Thr Leu Pro Phe Gln Arg Leu Arg Arg Asn Thr Leu
145                 150                 155                 160

Phe Val Asp Val Leu Ser Val Lys Glu Phe Ala Lys Thr Leu Leu Leu
                165                 170                 175

Gln Tyr Leu Pro Glu Asp Phe Asp Ile Leu Cys Thr His Pro Met Phe
            180                 185                 190

Gly Pro Gln Ser Val Ser Ser Asn His Gly Trp Arg Gly Leu Arg Phe
        195                 200                 205

Val Tyr Asp Lys Val Arg Ile Gly Glu Glu Arg Leu Arg Val Ser Arg
    210                 215                 220

Cys Glu Ser Phe Leu Glu Ile Phe Val Arg Glu Gly Cys Glu Met Val
225                 230                 235                 240

Glu Met Ser Val Thr Asp His Asp Lys Phe Ala Ala Glu Ser Gln Phe
                245                 250                 255

Ile Thr His Thr Leu Gly Arg Leu Leu Gly Met Leu Lys Leu Ile Ser
            260                 265                 270

Thr Pro Ile Asn Thr Lys Gly Tyr Glu Ala Leu Leu Asp Leu Ala Glu
```

```
                275                 280                 285
Asn Ile Cys Gly Asp Ser Phe Asp Leu Tyr Tyr Gly Leu Phe Val Tyr
290                 295                 300

Asn Asn Asn Ser Leu Glu Val Leu Glu Arg Ile Asp Leu Ala Phe Glu
305                 310                 315                 320

Ala Leu Arg Lys Glu Leu Phe Ser Arg Leu His Gly Val Val Arg Lys
                325                 330                 335

Gln Ser Phe Glu Gly Glu Ala Lys Lys Val His Val Phe Pro Asn Cys
                340                 345                 350

Gly Glu Asn Asp Ala Ser Leu Asp Met Met Arg Ser Glu Asp Val Val
                355                 360                 365

Val Lys Tyr Glu Tyr Asn Ser Gln Val Ser Gly Ser Val Asn Asp Gly
370                 375                 380

Ser Arg Leu Lys Ile Gly Ile Val Gly Phe Gly Asn Phe Gly Gln Phe
385                 390                 395                 400

Leu Gly Lys Thr Met Val Lys Gln Gly His Thr Val Leu Ala Tyr Ser
                405                 410                 415

Arg Ser Asp Tyr Thr Asp Glu Ala Ala Lys Leu Gly Val Ser Tyr Phe
                420                 425                 430

Ser Asp Leu Asp Asp Leu Phe Glu Glu His Pro Glu Val Ile Ile Leu
                435                 440                 445

Cys Thr Ser Ile Leu Ser Thr Glu Lys Val Leu Glu Ser Leu Pro Phe
                450                 455                 460

Gln Arg Leu Lys Arg Ser Thr Leu Phe Val Asp Val Leu Ser Val Lys
465                 470                 475                 480

Glu Phe Pro Arg Asn Leu Phe Leu Gln Thr Leu Pro Gln Asp Phe Asp
                485                 490                 495

Ile Leu Cys Thr His Pro Met Phe Gly Pro Glu Ser Gly Lys Asn Gly
                500                 505                 510

Trp Asn Asn Leu Ala Phe Val Phe Asp Lys Val Arg Ile Gly Met Asp
                515                 520                 525

Asp Arg Arg Lys Ser Arg Cys Asn Ser Phe Leu Asp Ile Phe Ala Arg
530                 535                 540

Glu Gly Cys Arg Met Val Glu Met Ser Cys Ala Glu His Asp Trp His
545                 550                 555                 560

Ala Ala Gly Ser Gln Phe Ile Thr His Thr Val Gly Arg Leu Leu Glu
                565                 570                 575

Lys Leu Ser Leu Glu Ser Thr Pro Ile Asp Thr Lys Gly Tyr Glu Thr
                580                 585                 590

Leu Leu Lys Leu Val Glu Asn Thr Ala Gly Asp Ser Phe Asp Leu Tyr
                595                 600                 605

Tyr Gly Leu Phe Leu Tyr Asn Pro Asn Ala Met Glu Gln Leu Glu Arg
                610                 615                 620

Phe His Val Ala Phe Glu Ser Leu Lys Thr Gln Leu Phe Gly Arg Leu
625                 630                 635                 640

His Ser Gln His Ser His Glu Leu Ala Lys Ser Ser Pro Lys Thr
                645                 650                 655

Thr Lys Leu Leu
            660

<210> SEQ ID NO 4
<211> LENGTH: 933
<212> TYPE: DNA
<213> ORGANISM: Arabidopsis thaliana
```

```
<220> FEATURE:
<221> NAME/KEY: CDS
<222> LOCATION: (1)..(933)

<400> SEQUENCE: 4 atg acc gac acc atc cct ctt ccc aac tcc aac tcc aac gcc acc cct      48
Met Thr Asp Thr Ile Pro Leu Pro Asn Ser Asn Ser Asn Ala Thr Pro
1               5                   10                  15 cct ctc cgt atc gcc atc atc gga ttc gga aac tac ggc caa ttc ctt      96
Pro Leu Arg Ile Ala Ile Ile Gly Phe Gly Asn Tyr Gly Gln Phe Leu
            20                  25                  30 gcc gaa acc cta att tct caa ggc cac att ctc ttc gct cac tcc cga     144
Ala Glu Thr Leu Ile Ser Gln Gly His Ile Leu Phe Ala His Ser Arg
        35                  40                  45 tcc gat cac tcc tcc gcc gct cgc cgt ctc ggt gtc tca tac ttc acc     192
Ser Asp His Ser Ser Ala Ala Arg Arg Leu Gly Val Ser Tyr Phe Thr
    50                  55                  60 gat ctt cac gat ctc tgc gaa cgt cat cct gac gta gtc ctt ctc tgt     240
Asp Leu His Asp Leu Cys Glu Arg His Pro Asp Val Val Leu Leu Cys
65                  70                  75                  80 act tca atc ctc tcc ata gag aat att ctc aaa acg ttg ccg ttt cag     288
Thr Ser Ile Leu Ser Ile Glu Asn Ile Leu Lys Thr Leu Pro Phe Gln
                85                  90                  95 aga ctc cgt cgc aac act ctc ttc gtt gat gtt ctc tcc gtt aaa gag     336
Arg Leu Arg Arg Asn Thr Leu Phe Val Asp Val Leu Ser Val Lys Glu
            100                 105                 110 ttt gct aaa act ctt ctc ctt caa tac tta cct gaa gat ttc gat att     384
Phe Ala Lys Thr Leu Leu Leu Gln Tyr Leu Pro Glu Asp Phe Asp Ile
        115                 120                 125 ctt tgt aca cat cca atg ttt ggt cct cag agt gtg agt tca aat cat     432
Leu Cys Thr His Pro Met Phe Gly Pro Gln Ser Val Ser Ser Asn His
    130                 135                 140 ggc tgg aga gga tta aga ttt gtg tat gat aaa gtt agg att ggg gaa     480
Gly Trp Arg Gly Leu Arg Phe Val Tyr Asp Lys Val Arg Ile Gly Glu
145                 150                 155                 160 gag aga ttg aga gtc tca agg tgt gag agt ttt ctt gag att ttt gtt     528
Glu Arg Leu Arg Val Ser Arg Cys Glu Ser Phe Leu Glu Ile Phe Val
                165                 170                 175 aga gaa gga tgt gag atg gtg gag atg agt gtt act gat cat gat aag     576
Arg Glu Gly Cys Glu Met Val Glu Met Ser Val Thr Asp His Asp Lys
            180                 185                 190 ttt gct gct gaa tca cag ttt ata act cat act ctt ggt agg ctt ttg     624
Phe Ala Ala Glu Ser Gln Phe Ile Thr His Thr Leu Gly Arg Leu Leu
        195                 200                 205 ggg atg ttg aag ttg ata tcg acg ccg att aat acg aaa ggg tac gag     672
Gly Met Leu Lys Leu Ile Ser Thr Pro Ile Asn Thr Lys Gly Tyr Glu
    210                 215                 220 gcg ttg ctt gat tta gct gag aat att tgt ggg gat agt ttt gat ttg     720
Ala Leu Leu Asp Leu Ala Glu Asn Ile Cys Gly Asp Ser Phe Asp Leu
225                 230                 235                 240 tat tat ggg ttg ttt gtg tat aat aac aac tct ttg gag gtg tta gag     768
Tyr Tyr Gly Leu Phe Val Tyr Asn Asn Asn Ser Leu Glu Val Leu Glu
                245                 250                 255 agg att gat ttg gct ttc gag gct ttg cgt aag gag ctt ttt agt cgg     816
Arg Ile Asp Leu Ala Phe Glu Ala Leu Arg Lys Glu Leu Phe Ser Arg
            260                 265                 270 ctt cac ggt gtt gtg agg aag cag tct ttt gaa ggt gaa gca aag aaa     864
Leu His Gly Val Val Arg Lys Gln Ser Phe Glu Gly Glu Ala Lys Lys
        275                 280                 285 gtt cat gtt ttt cca aat tgt ggt gaa aat gat gct tct ttg gat atg     912
Val His Val Phe Pro Asn Cys Gly Glu Asn Asp Ala Ser Leu Asp Met
```

```
Val His Val Phe Pro Asn Cys Gly Glu Asn Asp Ala Ser Leu Asp Met
    290                 295                 300 atg agg tat gta gtt agt tag                                                     933
Met Arg Tyr Val Val Ser
305                 310
```

<210> SEQ ID NO 5
<211> LENGTH: 310
<212> TYPE: PRT
<213> ORGANISM: Arabidopsis thaliana

<400> SEQUENCE: 5

```
Met Thr Asp Thr Ile Pro Leu Pro Asn Ser Asn Ser Asn Ala Thr Pro
1               5                   10                  15

Pro Leu Arg Ile Ala Ile Ile Gly Phe Gly Asn Tyr Gly Gln Phe Leu
            20                  25                  30

Ala Glu Thr Leu Ile Ser Gln Gly His Ile Leu Phe Ala His Ser Arg
        35                  40                  45

Ser Asp His Ser Ser Ala Ala Arg Arg Leu Gly Val Ser Tyr Phe Thr
    50                  55                  60

Asp Leu His Asp Leu Cys Glu Arg His Pro Asp Val Val Leu Leu Cys
65                  70                  75                  80

Thr Ser Ile Leu Ser Ile Glu Asn Ile Leu Lys Thr Leu Pro Phe Gln
                85                  90                  95

Arg Leu Arg Arg Asn Thr Leu Phe Val Asp Val Leu Ser Val Lys Glu
            100                 105                 110

Phe Ala Lys Thr Leu Leu Leu Gln Tyr Leu Pro Glu Asp Phe Asp Ile
        115                 120                 125

Leu Cys Thr His Pro Met Phe Gly Pro Gln Ser Val Ser Ser Asn His
    130                 135                 140

Gly Trp Arg Gly Leu Arg Phe Val Tyr Asp Lys Val Arg Ile Gly Glu
145                 150                 155                 160

Glu Arg Leu Arg Val Ser Arg Cys Glu Ser Phe Leu Glu Ile Phe Val
                165                 170                 175

Arg Glu Gly Cys Glu Met Val Glu Met Ser Val Thr Asp His Asp Lys
            180                 185                 190

Phe Ala Ala Glu Ser Gln Phe Ile Thr His Thr Leu Gly Arg Leu Leu
        195                 200                 205

Gly Met Leu Lys Leu Ile Ser Thr Pro Ile Asn Thr Lys Gly Tyr Glu
    210                 215                 220

Ala Leu Leu Asp Leu Ala Glu Asn Ile Cys Gly Asp Ser Phe Asp Leu
225                 230                 235                 240

Tyr Tyr Gly Leu Phe Val Tyr Asn Asn Ser Leu Glu Val Leu Glu
                245                 250                 255

Arg Ile Asp Leu Ala Phe Glu Ala Leu Arg Lys Glu Leu Phe Ser Arg
            260                 265                 270

Leu His Gly Val Val Arg Lys Gln Ser Phe Glu Gly Glu Ala Lys Lys
        275                 280                 285

Val His Val Phe Pro Asn Cys Gly Glu Asn Asp Ala Ser Leu Asp Met
    290                 295                 300

Met Arg Tyr Val Val Ser
305                 310
```

<210> SEQ ID NO 6
<211> LENGTH: 909
<212> TYPE: DNA

<213> ORGANISM: Arabidopsis thaliana
<220> FEATURE:
<221> NAME/KEY: CDS
<222> LOCATION: (1)..(909)

<400> SEQUENCE: 6

```
atg atg agg tca gaa gat gtt gtt gtg aag tat gaa tat aac tcc cag        48
Met Met Arg Ser Glu Asp Val Val Val Lys Tyr Glu Tyr Asn Ser Gln
1               5                  10                  15 gtg tct ggt agt gtt aat gac ggt tcg agg ctc aag att ggt atc gtc        96
Val Ser Gly Ser Val Asn Asp Gly Ser Arg Leu Lys Ile Gly Ile Val
            20                  25                  30 ggg ttt gga aat ttt gga cag ttt cta ggt aaa acc atg gtc aag cag       144
Gly Phe Gly Asn Phe Gly Gln Phe Leu Gly Lys Thr Met Val Lys Gln
        35                  40                  45 ggt cac act gtg tta gct tat tcc aga agt gac tac act gat gaa gca       192
Gly His Thr Val Leu Ala Tyr Ser Arg Ser Asp Tyr Thr Asp Glu Ala
    50                  55                  60 gca aag ctc ggt gtt tcg tat ttt tca gat ctt gat gat cta ttt gaa       240
Ala Lys Leu Gly Val Ser Tyr Phe Ser Asp Leu Asp Asp Leu Phe Glu
65                  70                  75                  80 gag cat cct gaa gtt att att ctc tgt acg tca atc ctt tcg act gaa       288
Glu His Pro Glu Val Ile Ile Leu Cys Thr Ser Ile Leu Ser Thr Glu
                85                  90                  95 aaa gtt ctc gag tca cta ccg ttt cag aga ctg aag aga agc aca ctt       336
Lys Val Leu Glu Ser Leu Pro Phe Gln Arg Leu Lys Arg Ser Thr Leu
            100                 105                 110 ttt gtg gat gta ctc tca gta aaa gag ttc ccg agg aat tta ttt ctt       384
Phe Val Asp Val Leu Ser Val Lys Glu Phe Pro Arg Asn Leu Phe Leu
        115                 120                 125 caa act ctc cca caa gat ttt gat att ttg tgc acg cat cct atg ttt       432
Gln Thr Leu Pro Gln Asp Phe Asp Ile Leu Cys Thr His Pro Met Phe
    130                 135                 140 ggg cca gag agt ggt aaa aat gga tgg aac aat ctt gcc ttt gtg ttt       480
Gly Pro Glu Ser Gly Lys Asn Gly Trp Asn Asn Leu Ala Phe Val Phe
145                 150                 155                 160 gat aag gtt agg att gga atg gat gat aga aga aaa tcg agg tgt aac       528
Asp Lys Val Arg Ile Gly Met Asp Asp Arg Arg Lys Ser Arg Cys Asn
                165                 170                 175 agt ttt ctt gat att ttt gcc cgt gaa gga tgt cgt atg gtg gag atg       576
Ser Phe Leu Asp Ile Phe Ala Arg Glu Gly Cys Arg Met Val Glu Met
            180                 185                 190 tcg tgt gct gaa cat gat tgg cat gct gct gga tca cag ttt atc aca       624
Ser Cys Ala Glu His Asp Trp His Ala Ala Gly Ser Gln Phe Ile Thr
        195                 200                 205 cac aca gtg gga agg ctt ctg gag aag ctg agc ttg gaa tct act cct       672
His Thr Val Gly Arg Leu Leu Glu Lys Leu Ser Leu Glu Ser Thr Pro
    210                 215                 220 ata gat acc aaa ggt tat gag aca ttg cta aaa ctg gtg gag aat act       720
Ile Asp Thr Lys Gly Tyr Glu Thr Leu Leu Lys Leu Val Glu Asn Thr
225                 230                 235                 240 gct ggt gac agc ttt gat ctg tac tat gga cta ttt tta tac aat cct       768
Ala Gly Asp Ser Phe Asp Leu Tyr Tyr Gly Leu Phe Leu Tyr Asn Pro
                245                 250                 255 aat gca atg gaa cag ctt gag agg ttt cat gtg gct ttt gaa tca ttg       816
Asn Ala Met Glu Gln Leu Glu Arg Phe His Val Ala Phe Glu Ser Leu
            260                 265                 270 aag aca cag ctc ttt gga cga cta cat tct caa cat tct cat gag cta       864
Lys Thr Gln Leu Phe Gly Arg Leu His Ser Gln His Ser His Glu Leu
        275                 280                 285
```

```
gct aaa tca tct tcc cca aag aca act aag cta tta act agc taa          909
Ala Lys Ser Ser Ser Pro Lys Thr Thr Lys Leu Leu Thr Ser
    290             295                 300
```

<210> SEQ ID NO 7
<211> LENGTH: 302
<212> TYPE: PRT
<213> ORGANISM: Arabidopsis thaliana

<400> SEQUENCE: 7

```
Met Met Arg Ser Glu Asp Val Val Lys Tyr Glu Tyr Asn Ser Gln
1               5                   10                  15

Val Ser Gly Ser Val Asn Asp Gly Ser Arg Leu Lys Ile Gly Ile Val
            20                  25                  30

Gly Phe Gly Asn Phe Gly Gln Phe Leu Gly Lys Thr Met Val Lys Gln
            35                  40                  45

Gly His Thr Val Leu Ala Tyr Ser Arg Ser Asp Tyr Thr Asp Glu Ala
        50                  55                  60

Ala Lys Leu Gly Val Ser Tyr Phe Ser Asp Leu Asp Asp Leu Phe Glu
65                  70                  75                  80

Glu His Pro Glu Val Ile Ile Leu Cys Thr Ser Ile Leu Ser Thr Glu
                85                  90                  95

Lys Val Leu Glu Ser Leu Pro Phe Gln Arg Leu Lys Arg Ser Thr Leu
            100                 105                 110

Phe Val Asp Val Leu Ser Val Lys Glu Phe Pro Arg Asn Leu Phe Leu
        115                 120                 125

Gln Thr Leu Pro Gln Asp Phe Asp Ile Leu Cys Thr His Pro Met Phe
    130                 135                 140

Gly Pro Glu Ser Gly Lys Asn Gly Trp Asn Asn Leu Ala Phe Val Phe
145                 150                 155                 160

Asp Lys Val Arg Ile Gly Met Asp Asp Arg Arg Lys Ser Arg Cys Asn
                165                 170                 175

Ser Phe Leu Asp Ile Phe Ala Arg Glu Gly Cys Arg Met Val Glu Met
            180                 185                 190

Ser Cys Ala Glu His Asp Trp His Ala Ala Gly Ser Gln Phe Ile Thr
        195                 200                 205

His Thr Val Gly Arg Leu Leu Glu Lys Leu Ser Leu Glu Ser Thr Pro
    210                 215                 220

Ile Asp Thr Lys Gly Tyr Glu Thr Leu Leu Lys Leu Val Glu Asn Thr
225                 230                 235                 240

Ala Gly Asp Ser Phe Asp Leu Tyr Tyr Gly Leu Phe Leu Tyr Asn Pro
                245                 250                 255

Asn Ala Met Glu Gln Leu Glu Arg Phe His Val Ala Phe Glu Ser Leu
            260                 265                 270

Lys Thr Gln Leu Phe Gly Arg Leu His Ser Gln His Ser His Glu Leu
        275                 280                 285

Ala Lys Ser Ser Ser Pro Lys Thr Thr Lys Leu Leu Thr Ser
    290                 295                 300
```

<210> SEQ ID NO 8
<211> LENGTH: 1077
<212> TYPE: DNA
<213> ORGANISM: Arabidopsis thaliana
<220> FEATURE:
<221> NAME/KEY: CDS
<222> LOCATION: (1)..(1077)

<400> SEQUENCE: 8

```
atg cta ctc cat ttc tct ccg gcg aaa ccc ctc att tct cca ccc aat      48
Met Leu Leu His Phe Ser Pro Ala Lys Pro Leu Ile Ser Pro Pro Asn
1               5                   10                  15 ctc cgc cgc aat tca ccc aca ttc ctc att tcc ccg ccg cga tct ctt      96
Leu Arg Arg Asn Ser Pro Thr Phe Leu Ile Ser Pro Pro Arg Ser Leu
            20                  25                  30 cga att cga gca atc gac gcc gcc caa atc ttc gat tac gaa acc caa     144
Arg Ile Arg Ala Ile Asp Ala Ala Gln Ile Phe Asp Tyr Glu Thr Gln
        35                  40                  45 ctc aaa tcc gag tac cgc aaa tcc tct gct ctc aaa atc gcc gtc ttg     192
Leu Lys Ser Glu Tyr Arg Lys Ser Ser Ala Leu Lys Ile Ala Val Leu
    50                  55                  60 ggt ttc ggc aat ttc ggc caa ttc ctc tcc aaa acc cta att cga cac     240
Gly Phe Gly Asn Phe Gly Gln Phe Leu Ser Lys Thr Leu Ile Arg His
65                  70                  75                  80 ggc cac gat cta atc act cac tcc cgc tcc gat tac tcc gac gcc gca     288
Gly His Asp Leu Ile Thr His Ser Arg Ser Asp Tyr Ser Asp Ala Ala
                85                  90                  95 aac tca atc gga gct cgt ttc ttc gat aac cct cac gat ctc tgt gaa     336
Asn Ser Ile Gly Ala Arg Phe Phe Asp Asn Pro His Asp Leu Cys Glu
            100                 105                 110 caa cat ccc gac gtt gtc ctc ctc tgt acc tca atc ctc tcc aca gaa     384
Gln His Pro Asp Val Val Leu Leu Cys Thr Ser Ile Leu Ser Thr Glu
        115                 120                 125 tca gtc ctc aga tca ttc cct ttc caa cgt ctc cgt cgt agc aca ctc     432
Ser Val Leu Arg Ser Phe Pro Phe Gln Arg Leu Arg Arg Ser Thr Leu
    130                 135                 140 ttc gtc gat gtt ctc tcc gtt aag gaa ttc cca aaa gcc ctc ttc att     480
Phe Val Asp Val Leu Ser Val Lys Glu Phe Pro Lys Ala Leu Phe Ile
145                 150                 155                 160 aaa tac ctt cct aag gag ttt gac att ctc tgt act cat cca atg ttt     528
Lys Tyr Leu Pro Lys Glu Phe Asp Ile Leu Cys Thr His Pro Met Phe
                165                 170                 175 gga cct gag agt ggt aag cat tct tgg tct ggc ttg ccc ttt gtc tac     576
Gly Pro Glu Ser Gly Lys His Ser Trp Ser Gly Leu Pro Phe Val Tyr
            180                 185                 190 gat aag gtg aga atc gga gac gca gct tca aga caa gag agg tgt gag     624
Asp Lys Val Arg Ile Gly Asp Ala Ala Ser Arg Gln Glu Arg Cys Glu
        195                 200                 205 aag ttt cta aga att ttt gag aat gaa ggt tgc aag atg gtt gaa atg     672
Lys Phe Leu Arg Ile Phe Glu Asn Glu Gly Cys Lys Met Val Glu Met
    210                 215                 220 agc tgt gag aag cat gat tat tac gca gct gga tcg caa ttc gtg acg     720
Ser Cys Glu Lys His Asp Tyr Tyr Ala Ala Gly Ser Gln Phe Val Thr
225                 230                 235                 240 cat act atg gga agg gtt ttg gag aaa tat gga gtt gag tct tcg ccg     768
His Thr Met Gly Arg Val Leu Glu Lys Tyr Gly Val Glu Ser Ser Pro
                245                 250                 255 att aac acc aaa ggt tat gag acg ttg ttg gat ttg gtg gag aac aca     816
Ile Asn Thr Lys Gly Tyr Glu Thr Leu Leu Asp Leu Val Glu Asn Thr
            260                 265                 270 tcg agt gat agc ttt gag ctt ttc tac ggt ttg ttt atg tat aat ccg     864
Ser Ser Asp Ser Phe Glu Leu Phe Tyr Gly Leu Phe Met Tyr Asn Pro
        275                 280                 285 aat gct ctt gaa cag ttg gag aga ttg gat atg gct ttt gag tct gtt     912
Asn Ala Leu Glu Gln Leu Glu Arg Leu Asp Met Ala Phe Glu Ser Val
    290                 295                 300 aag aag gag ctg ttt ggg aga tta cat cag caa tac agg aag caa atg     960
Lys Lys Glu Leu Phe Gly Arg Leu His Gln Gln Tyr Arg Lys Gln Met
```

```
                305                 310                 315                 320
ttt ggt ggg gag gtt caa tcg ccc aag aaa act gag cag aaa ttg ctc        1008
Phe Gly Gly Glu Val Gln Ser Pro Lys Lys Thr Glu Gln Lys Leu Leu
                325                 330                 335 aat gat ggt ggt gtt gtt cct atg aat gat ata tca tca tca tca            1056
Asn Asp Gly Gly Val Val Pro Met Asn Asp Ile Ser Ser Ser Ser
            340                 345                 350 tca tca tca tca tca tct taa                                            1077
Ser Ser Ser Ser Ser Ser
        355

<210> SEQ ID NO 9
<211> LENGTH: 358
<212> TYPE: PRT
<213> ORGANISM: Arabidopsis thaliana

<400> SEQUENCE: 9

Met Leu Leu His Phe Ser Pro Ala Lys Pro Leu Ile Ser Pro Pro Asn
1               5                   10                  15

Leu Arg Arg Asn Ser Pro Thr Phe Leu Ile Ser Pro Arg Ser Leu
            20                  25                  30

Arg Ile Arg Ala Ile Asp Ala Ala Gln Ile Phe Asp Tyr Glu Thr Gln
        35                  40                  45

Leu Lys Ser Glu Tyr Arg Lys Ser Ser Ala Leu Lys Ile Ala Val Leu
    50                  55                  60

Gly Phe Gly Asn Phe Gly Gln Phe Leu Ser Lys Thr Leu Ile Arg His
65                  70                  75                  80

Gly His Asp Leu Ile Thr His Ser Arg Ser Asp Tyr Ser Asp Ala Ala
                85                  90                  95

Asn Ser Ile Gly Ala Arg Phe Phe Asp Asn Pro His Asp Leu Cys Glu
            100                 105                 110

Gln His Pro Asp Val Val Leu Leu Cys Thr Ser Ile Leu Ser Thr Glu
        115                 120                 125

Ser Val Leu Arg Ser Phe Pro Phe Gln Arg Leu Arg Arg Ser Thr Leu
    130                 135                 140

Phe Val Asp Val Leu Ser Val Lys Glu Phe Pro Lys Ala Leu Phe Ile
145                 150                 155                 160

Lys Tyr Leu Pro Lys Glu Phe Asp Ile Leu Cys Thr His Pro Met Phe
                165                 170                 175

Gly Pro Glu Ser Gly Lys His Ser Trp Ser Gly Leu Pro Phe Val Tyr
            180                 185                 190

Asp Lys Val Arg Ile Gly Asp Ala Ala Ser Arg Gln Glu Arg Cys Glu
        195                 200                 205

Lys Phe Leu Arg Ile Phe Glu Asn Glu Gly Cys Lys Met Val Glu Met
    210                 215                 220

Ser Cys Glu Lys His Asp Tyr Tyr Ala Ala Gly Ser Gln Phe Val Thr
225                 230                 235                 240

His Thr Met Gly Arg Val Leu Glu Lys Tyr Gly Val Glu Ser Ser Pro
                245                 250                 255

Ile Asn Thr Lys Gly Tyr Glu Thr Leu Leu Asp Leu Val Glu Asn Thr
            260                 265                 270

Ser Ser Asp Ser Phe Glu Leu Phe Tyr Gly Leu Phe Tyr Asn Pro
        275                 280                 285

Asn Ala Leu Glu Gln Leu Glu Arg Leu Asp Met Ala Phe Glu Ser Val
    290                 295                 300
```

```
Lys Lys Glu Leu Phe Gly Arg Leu His Gln Gln Tyr Arg Lys Gln Met
305                 310                 315                 320

Phe Gly Gly Glu Val Gln Ser Pro Lys Lys Thr Glu Gln Lys Leu Leu
                325                 330                 335

Asn Asp Gly Gly Val Val Pro Met Asn Asp Ile Ser Ser Ser Ser
            340                 345                 350

Ser Ser Ser Ser Ser Ser
        355
```

<210> SEQ ID NO 10
<211> LENGTH: 1476
<212> TYPE: DNA
<213> ORGANISM: Picea glauca
<220> FEATURE:
<221> NAME/KEY: CDS
<222> LOCATION: (96)..(980)

<400> SEQUENCE: 10

```
accagtttta gatattcatc aaggtcttgc ctgctttgtt ttaggcaatt ccctccagta      60
ccaagccctc ttctcagaaa actccctccg cggca atg cct ctt cat ttc tca       113
                                        Met Pro Leu His Phe Ser
                                          1               5 tgg aat cca aca gaa gac cct cac aca gta cgc cct act gag gct ctc      161
Trp Asn Pro Thr Glu Asp Pro His Thr Val Arg Pro Thr Glu Ala Leu
             10                  15                  20 agg aat cag agc aat gga cgt cgc ggg gcc cct cga tta aga aga ata      209
Arg Asn Gln Ser Asn Gly Arg Arg Gly Ala Pro Arg Leu Arg Arg Ile
         25                  30                  35 aaa tcc att aaa tat tgg cat cgt agg gtt tgg aaa cta cca cca att      257
Lys Ser Ile Lys Tyr Trp His Arg Arg Val Trp Lys Leu Pro Pro Ile
 40                  45                  50 tct ggt gaa aac cat ggt gaa gcc ggg cca ccc ggt gct cgc cca ttc      305
Ser Gly Glu Asn His Gly Glu Ala Gly Pro Pro Gly Ala Arg Pro Phe
 55                  60                  65                  70 cag gac gga cta tac gga ggc cac tgc gag atc ggg gtt caa ttc ttc      353
Gln Asp Gly Leu Tyr Gly Gly His Cys Glu Ile Gly Val Gln Phe Phe
             75                  80                  85 aga gac gcg gac gat ttc tgc gaa gag cat cca gag atc ata ctg atg      401
Arg Asp Ala Asp Asp Phe Cys Glu Glu His Pro Glu Ile Ile Leu Met
         90                  95                 100 tgc gca tcc atc act ttg gtg gga gga cgt gct gaa gtc tct gcc aac      449
Cys Ala Ser Ile Thr Leu Val Gly Gly Arg Ala Glu Val Ser Ala Asn
        105                 110                 115 aca gcg cct gaa gag gag tac gct ttt cgc aga cgt cct gtc tgt gaa      497
Thr Ala Pro Glu Glu Glu Tyr Ala Phe Arg Arg Arg Pro Val Cys Glu
    120                 125                 130 aga gtt tcc gca ccg gtt gtt cct gca ggt ttt gtc gcc cga gtc gat      545
Arg Val Ser Ala Pro Val Val Pro Ala Gly Phe Val Ala Arg Val Asp
135                 140                 145                 150 gtg ctg tgc act cat ccc atg ttt ggt cca gag agc agc aag gac gat      593
Val Leu Cys Thr His Pro Met Phe Gly Pro Glu Ser Ser Lys Asp Asp
            155                 160                 165 ttg ggc gac ctc cct ttc gtt tac gat aag gtt agg gtt tct aac gaa      641
Leu Gly Asp Leu Pro Phe Val Tyr Asp Lys Val Arg Val Ser Asn Glu
        170                 175                 180 ggt ttg aga gcc aag cac tgc gag cgt ttt ctc aac ata ttt tcg tgc      689
Gly Leu Arg Ala Lys His Cys Glu Arg Phe Leu Asn Ile Phe Ser Cys
    185                 190                 195 gag ggc tgc cgg atg gtc gag atg tcg tgt gca gaa cat gat cgc tat      737
Glu Gly Cys Arg Met Val Glu Met Ser Cys Ala Glu His Asp Arg Tyr
```

-continued

```
                  200                 205                  210
gtc gcg gag agc caa ttc att acc cac acc gtt ggg agg atg ttg ggg    785
Val Ala Glu Ser Gln Phe Ile Thr His Thr Val Gly Arg Met Leu Gly
215                 220                  225                 230 agg ctg ggc ttg gag tcc act ccg att gct acc aag ggt tat gag aaa    833
Arg Leu Gly Leu Glu Ser Thr Pro Ile Ala Thr Lys Gly Tyr Glu Lys
                    235                 240                 245 tta ctg gaa gtg gcc tgg aat att gcc ggg gat agt ttt gat att tat    881
Leu Leu Glu Val Ala Trp Asn Ile Ala Gly Asp Ser Phe Asp Ile Tyr
        250                 255                 260 tat gga ctc ttc atg tat aat gtc aat tcg att gaa caa atc gag agg    929
Tyr Gly Leu Phe Met Tyr Asn Val Asn Ser Ile Glu Gln Ile Glu Arg
            265                 270                 275 tta gat atg gcg ttc aat tca ctc aag aac gag gtt tcg ggt tca aat    977
Leu Asp Met Ala Phe Asn Ser Leu Lys Asn Glu Val Ser Gly Ser Asn
        280                 285                 290 taa gaattttaaa ggtttcgatt tgcttgaagc ggcttgtgta tgaagtacca         1030
tttgtagaca ataatgaatt cgagaatgtt gttcaagatg aaatggttaa gaaggatggg  1090
tctcgtgtga gaagaaaacc aagataaatg gttgcgtagt ggtccagaaa tctgcattca  1150
ttactgaatg attctacatg gagtgagtaa gcattgattg aattccaaga cgagtgaaag  1210
agtttgatga atggaatatg tctgtattcc aaatttaata aatgaaaaat attgcaggtt  1270
gctatatgca atggttcttc tatatccccg aaggacaaat gacagatata agttctctgg  1330
cacttgtcag aaaacttcta tgtttgtagc cataaaacat tttccgaaag tggaactttt  1390
ctagaactta tagggggaaat aatccctatg caaacactgt atgagtccca ttgacctttc  1450
tttctcattt catttcattt ttgtct                                       1476
```

<210> SEQ ID NO 11
<211> LENGTH: 294
<212> TYPE: PRT
<213> ORGANISM: Picea glauca

<400> SEQUENCE: 11

```
Met Pro Leu His Phe Ser Trp Asn Pro Thr Glu Asp Pro His Thr Val
1               5                   10                  15

Arg Pro Thr Glu Ala Leu Arg Asn Gln Ser Asn Gly Arg Arg Gly Ala
            20                  25                  30

Pro Arg Leu Arg Arg Ile Lys Ser Ile Lys Tyr Trp His Arg Arg Val
        35                  40                  45

Trp Lys Leu Pro Pro Ile Ser Gly Glu Asn His Gly Glu Ala Gly Pro
    50                  55                  60

Pro Gly Ala Arg Pro Phe Gln Asp Gly Leu Tyr Gly Gly His Cys Glu
65                  70                  75                  80

Ile Gly Val Gln Phe Phe Arg Asp Ala Asp Phe Cys Glu Glu His
                85                  90                  95

Pro Glu Ile Ile Leu Met Cys Ala Ser Ile Thr Leu Val Gly Gly Arg
            100                 105                 110

Ala Glu Val Ser Ala Asn Thr Ala Pro Glu Glu Tyr Ala Phe Arg
        115                 120                 125

Arg Arg Pro Val Cys Glu Arg Val Ser Ala Pro Val Pro Ala Gly
    130                 135                 140

Phe Val Ala Arg Val Asp Val Leu Cys Thr His Pro Met Phe Gly Pro
145                 150                 155                 160

Glu Ser Ser Lys Asp Asp Leu Gly Asp Leu Pro Phe Val Tyr Asp Lys
                165                 170                 175
```

```
Val Arg Val Ser Asn Glu Gly Leu Arg Ala Lys His Cys Glu Arg Phe
            180                 185                 190

Leu Asn Ile Phe Ser Cys Glu Gly Cys Arg Met Val Glu Met Ser Cys
        195                 200                 205

Ala Glu His Asp Arg Tyr Val Ala Glu Ser Gln Phe Ile Thr His Thr
    210                 215                 220

Val Gly Arg Met Leu Gly Arg Leu Gly Leu Glu Ser Thr Pro Ile Ala
225                 230                 235                 240

Thr Lys Gly Tyr Glu Lys Leu Leu Glu Val Ala Trp Asn Ile Ala Gly
                245                 250                 255

Asp Ser Phe Asp Ile Tyr Tyr Gly Leu Phe Met Tyr Asn Val Asn Ser
            260                 265                 270

Ile Glu Gln Ile Glu Arg Leu Asp Met Ala Phe Asn Ser Leu Lys Asn
        275                 280                 285

Glu Val Ser Gly Ser Asn
    290
```

<210> SEQ ID NO 12
<211> LENGTH: 840
<212> TYPE: DNA
<213> ORGANISM: Synechocystis sp.
<220> FEATURE:
<221> NAME/KEY: CDS
<222> LOCATION: (1)..(840)

<400> SEQUENCE: 12

```
atg aaa att ggt gtt gtt ggt ttg ggt tta att ggg gct tcc ttg gcg      48
Met Lys Ile Gly Val Val Gly Leu Gly Leu Ile Gly Ala Ser Leu Ala
1               5                   10                  15 gga gac ttg cgt cgt cgg ggc cat tat ttg att ggg gtt tct cgg caa      96
Gly Asp Leu Arg Arg Arg Gly His Tyr Leu Ile Gly Val Ser Arg Gln
            20                  25                  30 caa agc acc tgt gaa aaa gca gtg gaa aga caa ttg gtg gat gaa gcg     144
Gln Ser Thr Cys Glu Lys Ala Val Glu Arg Gln Leu Val Asp Glu Ala
        35                  40                  45 ggt caa gat tta tct ctt ctc caa aca gca aaa ata att ttt ctt tgt     192
Gly Gln Asp Leu Ser Leu Leu Gln Thr Ala Lys Ile Ile Phe Leu Cys
    50                  55                  60 act cct ata caa tta att ttg cct acc cta gag aag ctt att ccc cat     240
Thr Pro Ile Gln Leu Ile Leu Pro Thr Leu Glu Lys Leu Ile Pro His
65                  70                  75                  80 cta tcg ccc aca gcc att gtc act gat gtg gcc tct gta aaa acg gcg     288
Leu Ser Pro Thr Ala Ile Val Thr Asp Val Ala Ser Val Lys Thr Ala
                85                  90                  95 atc gcc gag ccg gcc agt caa ctt tgg tct ggg ttc att ggt ggt cac     336
Ile Ala Glu Pro Ala Ser Gln Leu Trp Ser Gly Phe Ile Gly Gly His
            100                 105                 110 ccc atg gcc ggc aca gcg gcc cag ggc atc gac ggg gcg gaa gaa aat     384
Pro Met Ala Gly Thr Ala Ala Gln Gly Ile Asp Gly Ala Glu Glu Asn
        115                 120                 125 tta ttt gtc aac gct ccc tat gtg ctc act ccc acc gaa tat act gac     432
Leu Phe Val Asn Ala Pro Tyr Val Leu Thr Pro Thr Glu Tyr Thr Asp
    130                 135                 140 cca gag caa ttg gct tgt tta cgt tca gtg ttg gaa ccc ctg ggg gta     480
Pro Glu Gln Leu Ala Cys Leu Arg Ser Val Leu Glu Pro Leu Gly Val
145                 150                 155                 160 aaa att tac ctc tgc act ccc gca gac cat gac caa gca gta gcc tgg     528
Lys Ile Tyr Leu Cys Thr Pro Ala Asp His Asp Gln Ala Val Ala Trp
                165                 170                 175
```

```
att tcc cat tta cct gta atg gtg agt gct gct tta atc caa gcc tgt          576
Ile Ser His Leu Pro Val Met Val Ser Ala Ala Leu Ile Gln Ala Cys
        180                 185                 190 gcc ggt gaa aaa gat ggg gat att ctc aaa cta gcc caa aat ttg gcc          624
Ala Gly Glu Lys Asp Gly Asp Ile Leu Lys Leu Ala Gln Asn Leu Ala
            195                 200                 205 agt tcg ggt ttt cgg gat acc agt cgg gtg gga ggc ggc aac ccg gag          672
Ser Ser Gly Phe Arg Asp Thr Ser Arg Val Gly Gly Gly Asn Pro Glu
        210                 215                 220 ttg ggc acc atg atg gcc acc tat aac caa cgg gct ttg cta aaa agt          720
Leu Gly Thr Met Met Ala Thr Tyr Asn Gln Arg Ala Leu Leu Lys Ser
225                 230                 235                 240 ttg caa gac tat cgt cag cac ctg gat cag cta att acc cta att agt          768
Leu Gln Asp Tyr Arg Gln His Leu Asp Gln Leu Ile Thr Leu Ile Ser
                245                 250                 255 aac caa caa tgg cct gaa ctc cat cgt ctt tta caa caa acc aac ggc          816
Asn Gln Gln Trp Pro Glu Leu His Arg Leu Leu Gln Gln Thr Asn Gly
            260                 265                 270 gat cgg gac aag tat gtt gaa taa                                          840
Asp Arg Asp Lys Tyr Val Glu
        275

<210> SEQ ID NO 13
<211> LENGTH: 279
<212> TYPE: PRT
<213> ORGANISM: Synechocystis sp.

<400> SEQUENCE: 13

Met Lys Ile Gly Val Val Gly Leu Gly Leu Ile Gly Ala Ser Leu Ala
1               5                   10                  15

Gly Asp Leu Arg Arg Gly His Tyr Leu Ile Gly Val Ser Arg Gln
            20                  25                  30

Gln Ser Thr Cys Glu Lys Ala Val Glu Arg Gln Leu Val Asp Glu Ala
        35                  40                  45

Gly Gln Asp Leu Ser Leu Leu Gln Thr Ala Lys Ile Ile Phe Leu Cys
    50                  55                  60

Thr Pro Ile Gln Leu Ile Leu Pro Thr Leu Glu Lys Leu Ile Pro His
65                  70                  75                  80

Leu Ser Pro Thr Ala Ile Val Thr Asp Val Ala Ser Val Lys Thr Ala
                85                  90                  95

Ile Ala Glu Pro Ala Ser Gln Leu Trp Ser Gly Phe Ile Gly Gly His
            100                 105                 110

Pro Met Ala Gly Thr Ala Ala Gln Gly Ile Asp Gly Ala Glu Glu Asn
        115                 120                 125

Leu Phe Val Asn Ala Pro Tyr Val Leu Thr Pro Thr Glu Tyr Thr Asp
    130                 135                 140

Pro Glu Gln Leu Ala Cys Leu Arg Ser Val Leu Glu Pro Leu Gly Val
145                 150                 155                 160

Lys Ile Tyr Leu Cys Thr Pro Ala Asp His Asp Gln Ala Val Ala Trp
                165                 170                 175

Ile Ser His Leu Pro Val Met Val Ser Ala Ala Leu Ile Gln Ala Cys
            180                 185                 190

Ala Gly Glu Lys Asp Gly Asp Ile Leu Lys Leu Ala Gln Asn Leu Ala
        195                 200                 205

Ser Ser Gly Phe Arg Asp Thr Ser Arg Val Gly Gly Gly Asn Pro Glu
    210                 215                 220
```

```
Leu Gly Thr Met Met Ala Thr Tyr Asn Gln Arg Ala Leu Leu Lys Ser
225                 230                 235                 240

Leu Gln Asp Tyr Arg Gln His Leu Asp Gln Leu Ile Thr Leu Ile Ser
            245                 250                 255

Asn Gln Gln Trp Pro Glu Leu His Arg Leu Leu Gln Gln Thr Asn Gly
        260                 265                 270

Asp Arg Asp Lys Tyr Val Glu
            275

<210> SEQ ID NO 14
<211> LENGTH: 1359
<212> TYPE: DNA
<213> ORGANISM: Saccharomyces cerevisiae
<220> FEATURE:
<221> NAME/KEY: CDS
<222> LOCATION: (1)..(1359)

<400> SEQUENCE: 14 atg gta tca gag gat aag att gag caa tgg aaa gcc aca aaa gtc att      48
Met Val Ser Glu Asp Lys Ile Glu Gln Trp Lys Ala Thr Lys Val Ile
1               5                   10                  15 ggt ata att ggt ctg ggt gat atg ggc cta tta tac gct aat aaa ttt      96
Gly Ile Ile Gly Leu Gly Asp Met Gly Leu Leu Tyr Ala Asn Lys Phe
            20                  25                  30 aca gat gct gga tgg ggt gtt ata tgt tgt gat agg gaa gaa tat tat     144
Thr Asp Ala Gly Trp Gly Val Ile Cys Cys Asp Arg Glu Glu Tyr Tyr
        35                  40                  45 gat gaa ctg aaa gaa aaa tat gcc tca gct aaa ttc gaa ctg gtg aaa     192
Asp Glu Leu Lys Glu Lys Tyr Ala Ser Ala Lys Phe Glu Leu Val Lys
    50                  55                  60 aat ggt cat ttg gta tcc agg caa agc gac tat att atc tat agt gtt     240
Asn Gly His Leu Val Ser Arg Gln Ser Asp Tyr Ile Ile Tyr Ser Val
65                  70                  75                  80 gaa gca tcc aat att agt aag atc gtc gca acg tat gga cca tct tct     288
Glu Ala Ser Asn Ile Ser Lys Ile Val Ala Thr Tyr Gly Pro Ser Ser
                85                  90                  95 aag gtt gga aca att gtt ggg ggt caa acg agt tgt aag ctg ccg gaa     336
Lys Val Gly Thr Ile Val Gly Gly Gln Thr Ser Cys Lys Leu Pro Glu
            100                 105                 110 atc gag gct ttc gaa aag tat tta ccc aag gac tgc gac atc att acc     384
Ile Glu Ala Phe Glu Lys Tyr Leu Pro Lys Asp Cys Asp Ile Ile Thr
        115                 120                 125 gtg cat tcc ctt cat ggg cct aaa gtt aat act gaa ggc caa cca cta     432
Val His Ser Leu His Gly Pro Lys Val Asn Thr Glu Gly Gln Pro Leu
    130                 135                 140 gtt att atc aat cac aga tca cag tac cca gaa tct ttt gag ttc gtt     480
Val Ile Ile Asn His Arg Ser Gln Tyr Pro Glu Ser Phe Glu Phe Val
145                 150                 155                 160 aat tct gtt atg gca tgt ttg aaa agt aag caa gtt tat ttg aca tat     528
Asn Ser Val Met Ala Cys Leu Lys Ser Lys Gln Val Tyr Leu Thr Tyr
                165                 170                 175 gaa gag cat gac aag att acc gct gat aca caa gct gtg aca cat gct     576
Glu Glu His Asp Lys Ile Thr Ala Asp Thr Gln Ala Val Thr His Ala
            180                 185                 190 gct ttc tta agt atg gga tct gcg tgg gca aag ata aag att tat cct     624
Ala Phe Leu Ser Met Gly Ser Ala Trp Ala Lys Ile Lys Ile Tyr Pro
        195                 200                 205 tgg act ctg ggt gta aac aaa tgg tac ggt ggc cta gaa aat gtg aaa     672
Trp Thr Leu Gly Val Asn Lys Trp Tyr Gly Gly Leu Glu Asn Val Lys
    210                 215                 220
```

-continued

| | | |
|---|---|---|
| gtt aat ata tca cta aga atc tat tcg aac aag tgg cat gtt tac gca<br>Val Asn Ile Ser Leu Arg Ile Tyr Ser Asn Lys Trp His Val Tyr Ala<br>225                      230                   235                    240 | 720 |
| gga tta gcc ata aca aac cca agt gca cat cag caa att ctt caa tat<br>Gly Leu Ala Ile Thr Asn Pro Ser Ala His Gln Gln Ile Leu Gln Tyr<br>                  245                   250                   255 | 768 |
| gca acc agt gca aca gaa cta ttt agt tta atg ata gat aac aaa gaa<br>Ala Thr Ser Ala Thr Glu Leu Phe Ser Leu Met Ile Asp Asn Lys Glu<br>260                      265                   270 | 816 |
| caa gaa ctt act gat aga cta tta aaa gct aag caa ttt gta ttt gga<br>Gln Glu Leu Thr Asp Arg Leu Leu Lys Ala Lys Gln Phe Val Phe Gly<br>                  275                   280                   285 | 864 |
| aag cat act ggt ctc tta cta ttg gat gac acg att tta gag aaa tat<br>Lys His Thr Gly Leu Leu Leu Asp Asp Thr Ile Leu Glu Lys Tyr<br>290                      295                   300 | 912 |
| tcg cta tca aaa agc agc att ggt aac agc aac aat tgc aag cca gtg<br>Ser Leu Ser Lys Ser Ser Ile Gly Asn Ser Asn Asn Cys Lys Pro Val<br>305                      310                   315                   320 | 960 |
| ccg aat tca cat tta tca ttg ttg gcg att gtt gat tcg tgg ttt caa<br>Pro Asn Ser His Leu Ser Leu Leu Ala Ile Val Asp Ser Trp Phe Gln<br>                  325                   330                   335 | 1008 |
| ctt ggt att gat cca tat gat cat atg att tgt tcg acg cca tta ttc<br>Leu Gly Ile Asp Pro Tyr Asp His Met Ile Cys Ser Thr Pro Leu Phe<br>340                      345                   350 | 1056 |
| aga ata ttc ctg ggt gtg tcc gaa tat ctt ttt tta aaa cct ggc tta<br>Arg Ile Phe Leu Gly Val Ser Glu Tyr Leu Phe Leu Lys Pro Gly Leu<br>                  355                   360                   365 | 1104 |
| tta gaa cag aca att gat gca gct atc cat gat aaa tca ttc ata aaa<br>Leu Glu Gln Thr Ile Asp Ala Ala Ile His Asp Lys Ser Phe Ile Lys<br>370                      375                   380 | 1152 |
| gat gat tta gaa ttt gtt att tcg gct aga gaa tgg agc tcg gtt gtt<br>Asp Asp Leu Glu Phe Val Ile Ser Ala Arg Glu Trp Ser Ser Val Val<br>385                      390                   395                   400 | 1200 |
| tct ttt gcc aat ttt gat ata tac aaa aag caa ttt cag agt gtt caa<br>Ser Phe Ala Asn Phe Asp Ile Tyr Lys Lys Gln Phe Gln Ser Val Gln<br>                  405                   410                   415 | 1248 |
| aag ttc ttt gag cca atg ctt cca gag gct aat ctc att ggc aac gag<br>Lys Phe Phe Glu Pro Met Leu Pro Glu Ala Asn Leu Ile Gly Asn Glu<br>420                      425                   430 | 1296 |
| atg ata aaa acc att ctg agt cat tct agt gac cgt tcg gcc gct gaa<br>Met Ile Lys Thr Ile Leu Ser His Ser Ser Asp Arg Ser Ala Ala Glu<br>                  435                   440                   445 | 1344 |
| aaa aga aat aca taa<br>Lys Arg Asn Thr<br>    450 | 1359 |

<210> SEQ ID NO 15
<211> LENGTH: 452
<212> TYPE: PRT
<213> ORGANISM: Saccharomyces cerevisiae

<400> SEQUENCE: 15

Met Val Ser Glu Asp Lys Ile Glu Gln Trp Lys Ala Thr Lys Val Ile
1               5                   10                  15

Gly Ile Ile Gly Leu Gly Asp Met Gly Leu Leu Tyr Ala Asn Lys Phe
            20                  25                  30

Thr Asp Ala Gly Trp Gly Val Ile Cys Cys Asp Arg Glu Glu Tyr Tyr
        35                  40                  45

Asp Glu Leu Lys Glu Lys Tyr Ala Ser Ala Lys Phe Glu Leu Val Lys
    50                  55                  60

```
Asn Gly His Leu Val Ser Arg Gln Ser Asp Tyr Ile Ile Tyr Ser Val
 65                  70                  75                  80

Glu Ala Ser Asn Ile Ser Lys Ile Val Ala Thr Tyr Gly Pro Ser Ser
                 85                  90                  95

Lys Val Gly Thr Ile Val Gly Gly Gln Thr Ser Cys Lys Leu Pro Glu
            100                 105                 110

Ile Glu Ala Phe Glu Lys Tyr Leu Pro Lys Asp Cys Asp Ile Ile Thr
        115                 120                 125

Val His Ser Leu His Gly Pro Lys Val Asn Thr Glu Gly Gln Pro Leu
    130                 135                 140

Val Ile Ile Asn His Arg Ser Gln Tyr Pro Glu Ser Phe Glu Phe Val
145                 150                 155                 160

Asn Ser Val Met Ala Cys Leu Lys Ser Lys Gln Val Tyr Leu Thr Tyr
                165                 170                 175

Glu Glu His Asp Lys Ile Thr Ala Asp Thr Gln Ala Val Thr His Ala
            180                 185                 190

Ala Phe Leu Ser Met Gly Ser Ala Trp Ala Lys Ile Lys Ile Tyr Pro
        195                 200                 205

Trp Thr Leu Gly Val Asn Lys Trp Tyr Gly Gly Leu Glu Asn Val Lys
    210                 215                 220

Val Asn Ile Ser Leu Arg Ile Tyr Ser Asn Lys Trp His Val Tyr Ala
225                 230                 235                 240

Gly Leu Ala Ile Thr Asn Pro Ser Ala His Gln Gln Ile Leu Gln Tyr
                245                 250                 255

Ala Thr Ser Ala Thr Glu Leu Phe Ser Leu Met Ile Asp Asn Lys Glu
            260                 265                 270

Gln Glu Leu Thr Asp Arg Leu Leu Lys Ala Lys Gln Phe Val Phe Gly
        275                 280                 285

Lys His Thr Gly Leu Leu Leu Asp Asp Thr Ile Leu Glu Lys Tyr
    290                 295                 300

Ser Leu Ser Lys Ser Ser Ile Gly Asn Ser Asn Asn Cys Lys Pro Val
305                 310                 315                 320

Pro Asn Ser His Leu Ser Leu Ala Ile Val Asp Ser Trp Phe Gln
                325                 330                 335

Leu Gly Ile Asp Pro Tyr Asp His Met Ile Cys Ser Thr Pro Leu Phe
            340                 345                 350

Arg Ile Phe Leu Gly Val Ser Glu Tyr Leu Phe Leu Lys Pro Gly Leu
        355                 360                 365

Leu Glu Gln Thr Ile Asp Ala Ala Ile His Asp Lys Ser Phe Ile Lys
    370                 375                 380

Asp Asp Leu Glu Phe Val Ile Ser Ala Arg Glu Trp Ser Ser Val Val
385                 390                 395                 400

Ser Phe Ala Asn Phe Asp Ile Tyr Lys Lys Gln Phe Gln Ser Val Gln
                405                 410                 415

Lys Phe Phe Glu Pro Met Leu Pro Glu Ala Asn Leu Ile Gly Asn Glu
            420                 425                 430

Met Ile Lys Thr Ile Leu Ser His Ser Ser Asp Arg Ser Ala Ala Glu
        435                 440                 445

Lys Arg Asn Thr
    450

<210> SEQ ID NO 16
<211> LENGTH: 1116
```

```
<212> TYPE: DNA
<213> ORGANISM: Bacillus subtilis
<220> FEATURE:
<221> NAME/KEY: CDS
<222> LOCATION: (1)..(1116)

<400> SEQUENCE: 16 atg aat caa atg aaa gat aca ata ttg ctc gcc ggt ctc gga ttg ata      48
Met Asn Gln Met Lys Asp Thr Ile Leu Leu Ala Gly Leu Gly Leu Ile
1               5                   10                  15 ggc ggt tcg att gcc cta gcc atc aaa aaa aat cat ccc ggc aaa cgg      96
Gly Gly Ser Ile Ala Leu Ala Ile Lys Lys Asn His Pro Gly Lys Arg
            20                  25                  30 att atc gga atc gac atc tct gat gaa cag gcg gta gcg gca tta aaa     144
Ile Ile Gly Ile Asp Ile Ser Asp Glu Gln Ala Val Ala Ala Leu Lys
        35                  40                  45 tta ggc gtg ata gac gat cgt gct gat tcg ttt att agc ggt gtg aaa     192
Leu Gly Val Ile Asp Asp Arg Ala Asp Ser Phe Ile Ser Gly Val Lys
    50                  55                  60 gag gca gct aca gta atc att gcg aca cct gtt gaa caa aca ctg gtt     240
Glu Ala Ala Thr Val Ile Ile Ala Thr Pro Val Glu Gln Thr Leu Val
65                  70                  75                  80 atg ctt gaa gag ctg gct cat tca gga att gaa cat gag ctt ttg att     288
Met Leu Glu Glu Leu Ala His Ser Gly Ile Glu His Glu Leu Leu Ile
                85                  90                  95 acg gat gta gga agc aca aag caa aaa gtg gtt gat tac gct gat caa     336
Thr Asp Val Gly Ser Thr Lys Gln Lys Val Val Asp Tyr Ala Asp Gln
            100                 105                 110 gtg ctg cct agc cgc tat caa ttt gtc gga ggg cat ccg atg gcg ggt     384
Val Leu Pro Ser Arg Tyr Gln Phe Val Gly Gly His Pro Met Ala Gly
        115                 120                 125 tca cat aaa tca gga gtg gcc gct gcg aag gag ttc ctg ttt gaa aat     432
Ser His Lys Ser Gly Val Ala Ala Ala Lys Glu Phe Leu Phe Glu Asn
    130                 135                 140 gca ttt tat att tta acg cca ggc cag aaa acg gac aaa caa gct gtg     480
Ala Phe Tyr Ile Leu Thr Pro Gly Gln Lys Thr Asp Lys Gln Ala Val
145                 150                 155                 160 gaa cag tta aaa aac ctg ctg aag ggg acg aat gcc cat ttt gtg gaa     528
Glu Gln Leu Lys Asn Leu Leu Lys Gly Thr Asn Ala His Phe Val Glu
                165                 170                 175 atg tcg cca gag gag cat gat ggc gtt aca agc gta atc agt cat ttt     576
Met Ser Pro Glu Glu His Asp Gly Val Thr Ser Val Ile Ser His Phe
            180                 185                 190 ccg cat att gta gca gct agc ctt gtt cac caa acc cat cat tcg gaa     624
Pro His Ile Val Ala Ala Ser Leu Val His Gln Thr His His Ser Glu
        195                 200                 205 aac ctg tat ccg ctt gtt aag cgt ttt gct gcc ggc ggg ttc aga gat     672
Asn Leu Tyr Pro Leu Val Lys Arg Phe Ala Ala Gly Gly Phe Arg Asp
    210                 215                 220 att aca agg att gca tca agc agc ccg gca atg tgg cgg gat att tta     720
Ile Thr Arg Ile Ala Ser Ser Ser Pro Ala Met Trp Arg Asp Ile Leu
225                 230                 235                 240 tta cat aat aaa gat aaa atc tta gac cgt ttt gat gag tgg att cgt     768
Leu His Asn Lys Asp Lys Ile Leu Asp Arg Phe Asp Glu Trp Ile Arg
                245                 250                 255 gaa att gac aag atc cgt aca tat gta gaa caa gaa gat gcg gaa aat     816
Glu Ile Asp Lys Ile Arg Thr Tyr Val Glu Gln Glu Asp Ala Glu Asn
            260                 265                 270 cta ttt cgt tat ttt aaa aca gcc aag gat tat cgc gac ggg ctg ccg     864
Leu Phe Arg Tyr Phe Lys Thr Ala Lys Asp Tyr Arg Asp Gly Leu Pro
        275                 280                 285
```

```
ctt cgg cag aag gga gcg ata cct gca ttt tat gat tta tat gtg gat      912
Leu Arg Gln Lys Gly Ala Ile Pro Ala Phe Tyr Asp Leu Tyr Val Asp
    290                 295                 300 gta ccc gat cat ccg ggt gta ata tcc gag ata aca gcg atc tta gct      960
Val Pro Asp His Pro Gly Val Ile Ser Glu Ile Thr Ala Ile Leu Ala
305                 310                 315                 320 gcg gag cgc atc agt atc acg aat atc cgc att atc gaa aca cga gag     1008
Ala Glu Arg Ile Ser Ile Thr Asn Ile Arg Ile Ile Glu Thr Arg Glu
                325                 330                 335 gat att aac ggg att tta agg atc agt ttt cag tct gat gac gac cgc     1056
Asp Ile Asn Gly Ile Leu Arg Ile Ser Phe Gln Ser Asp Asp Asp Arg
            340                 345                 350 aaa agg gca gaa caa tgc att gaa gcc cgg gcg gaa tat gaa act ttt     1104
Lys Arg Ala Glu Gln Cys Ile Glu Ala Arg Ala Glu Tyr Glu Thr Phe
        355                 360                 365 tat gct gat tga                                                     1116
Tyr Ala Asp
    370

<210> SEQ ID NO 17
<211> LENGTH: 371
<212> TYPE: PRT
<213> ORGANISM: Bacillus subtilis

<400> SEQUENCE: 17

Met Asn Gln Met Lys Asp Thr Ile Leu Leu Ala Gly Leu Gly Leu Ile
1               5                   10                  15

Gly Gly Ser Ile Ala Leu Ala Ile Lys Lys Asn His Pro Gly Lys Arg
            20                  25                  30

Ile Ile Gly Ile Asp Ile Ser Asp Glu Gln Ala Val Ala Ala Leu Lys
        35                  40                  45

Leu Gly Val Ile Asp Asp Arg Ala Asp Ser Phe Ile Ser Gly Val Lys
    50                  55                  60

Glu Ala Ala Thr Val Ile Ile Ala Thr Pro Val Gln Thr Leu Val
65                  70                  75                  80

Met Leu Glu Glu Leu Ala His Ser Gly Ile Glu His Glu Leu Leu Ile
                85                  90                  95

Thr Asp Val Gly Ser Thr Lys Gln Lys Val Val Asp Tyr Ala Asp Gln
            100                 105                 110

Val Leu Pro Ser Arg Tyr Gln Phe Val Gly Gly His Pro Met Ala Gly
        115                 120                 125

Ser His Lys Ser Gly Val Ala Ala Lys Glu Phe Leu Phe Glu Asn
    130                 135                 140

Ala Phe Tyr Ile Leu Thr Pro Gly Gln Lys Thr Asp Lys Gln Ala Val
145                 150                 155                 160

Glu Gln Leu Lys Asn Leu Leu Lys Gly Thr Asn Ala His Phe Val Glu
                165                 170                 175

Met Ser Pro Glu Glu His Asp Gly Val Thr Ser Val Ile Ser His Phe
            180                 185                 190

Pro His Ile Val Ala Ala Ser Leu Val His Gln Thr His His Ser Glu
        195                 200                 205

Asn Leu Tyr Pro Leu Val Lys Arg Phe Ala Ala Gly Gly Phe Arg Asp
    210                 215                 220

Ile Thr Arg Ile Ala Ser Ser Pro Ala Met Trp Arg Asp Ile Leu
225                 230                 235                 240

Leu His Asn Lys Asp Lys Ile Leu Asp Arg Phe Asp Glu Trp Ile Arg
```

-continued

```
                    245                 250                 255
Glu Ile Asp Lys Ile Arg Thr Tyr Val Glu Gln Glu Asp Ala Glu Asn
                260                 265                 270

Leu Phe Arg Tyr Phe Lys Thr Ala Lys Asp Tyr Arg Asp Gly Leu Pro
            275                 280                 285

Leu Arg Gln Lys Gly Ala Ile Pro Ala Phe Tyr Asp Leu Tyr Val Asp
        290                 295                 300

Val Pro Asp His Pro Gly Val Ile Ser Glu Ile Thr Ala Ile Leu Ala
305                 310                 315                 320

Ala Glu Arg Ile Ser Ile Thr Asn Ile Arg Ile Ile Glu Thr Arg Glu
                325                 330                 335

Asp Ile Asn Gly Ile Leu Arg Ile Ser Phe Gln Ser Asp Asp Asp Arg
            340                 345                 350

Lys Arg Ala Glu Gln Cys Ile Glu Ala Arg Ala Glu Tyr Glu Thr Phe
        355                 360                 365

Tyr Ala Asp
    370

<210> SEQ ID NO 18
<211> LENGTH: 1122
<212> TYPE: DNA
<213> ORGANISM: Escherichia coli
<220> FEATURE:
<221> NAME/KEY: CDS
<222> LOCATION: (1)..(1122)

<400> SEQUENCE: 18 atg gtt gct gaa ttg acc gca tta cgc gat caa att gat gaa gtc gat        48
Met Val Ala Glu Leu Thr Ala Leu Arg Asp Gln Ile Asp Glu Val Asp
1               5                   10                  15 aaa gcg ctg ctg aat tta tta gcg aag cgt ctg gaa ctg gtt gct gaa        96
Lys Ala Leu Leu Asn Leu Leu Ala Lys Arg Leu Glu Leu Val Ala Glu
            20                  25                  30 gtg ggc gag gtg aaa agc cgc ttt gga ctg cct att tat gtt ccg gag       144
Val Gly Glu Val Lys Ser Arg Phe Gly Leu Pro Ile Tyr Val Pro Glu
        35                  40                  45 cgc gag gca tct atg ttg gcc tcg cgt cgt gca gag gcg gaa gct ctg       192
Arg Glu Ala Ser Met Leu Ala Ser Arg Arg Ala Glu Ala Glu Ala Leu
    50                  55                  60 ggt gta ccg cca gat ctg att gag gat gtt ttg cgt cgg gtg atg cgt       240
Gly Val Pro Pro Asp Leu Ile Glu Asp Val Leu Arg Arg Val Met Arg
65                  70                  75                  80 gaa tct tac tcc agt gaa aac gac aaa gga ttt aaa aca ctt tgt ccg       288
Glu Ser Tyr Ser Ser Glu Asn Asp Lys Gly Phe Lys Thr Leu Cys Pro
                85                  90                  95 tca ctg cgt ccg gtg gtt atc gtc ggc ggt ggc ggt cag atg gga cgc       336
Ser Leu Arg Pro Val Val Ile Val Gly Gly Gly Gly Gln Met Gly Arg
            100                 105                 110 ctg ttc gag aag atg ctg acc ctc tcg ggt tat cag gtg cgg att ctg       384
Leu Phe Glu Lys Met Leu Thr Leu Ser Gly Tyr Gln Val Arg Ile Leu
        115                 120                 125 gag caa cat gac tgg gat cga gcg gct gat att gtt gcc gat gcc gga       432
Glu Gln His Asp Trp Asp Arg Ala Ala Asp Ile Val Ala Asp Ala Gly
    130                 135                 140 atg gtg att gtt agt gtg cca atc cac gtt act gag caa gtt att ggc       480
Met Val Ile Val Ser Val Pro Ile His Val Thr Glu Gln Val Ile Gly
145                 150                 155                 160 aaa tta ccg cct tta ccg aaa gat tgt att ctg gtc gat ctg gca tca       528
Lys Leu Pro Pro Leu Pro Lys Asp Cys Ile Leu Val Asp Leu Ala Ser
```

-continued

```
                165                 170                 175
gtg aaa aat ggg cca tta cag gcc atg ctg gtg gcg cat gat ggt ccg    576
Val Lys Asn Gly Pro Leu Gln Ala Met Leu Val Ala His Asp Gly Pro
            180                 185                 190 gtg ctg ggg cta cac ccg atg ttc ggt ccg gac agc ggt agc ctg gca    624
Val Leu Gly Leu His Pro Met Phe Gly Pro Asp Ser Gly Ser Leu Ala
        195                 200                 205 aag caa gtt gtg gtc tgg tgt gat gga cgt aaa ccg gaa gca tac caa    672
Lys Gln Val Val Val Trp Cys Asp Gly Arg Lys Pro Glu Ala Tyr Gln
    210                 215                 220 tgg ttt ctg gag caa att cag gtc tgg ggc gct cgg ctg cat cgt att    720
Trp Phe Leu Glu Gln Ile Gln Val Trp Gly Ala Arg Leu His Arg Ile
225                 230                 235                 240 agc gcc gtc gag cac gat cag aat atg gcg ttt att cag gca ctg cgc    768
Ser Ala Val Glu His Asp Gln Asn Met Ala Phe Ile Gln Ala Leu Arg
                245                 250                 255 cac ttt gct act ttt gct tac ggg ctg cac ctg gca gaa gaa aat gtt    816
His Phe Ala Thr Phe Ala Tyr Gly Leu His Leu Ala Glu Glu Asn Val
            260                 265                 270 cag ctt gag caa ctt ctg gcg ctc tct tcg ccg att tac cgc ctt gag    864
Gln Leu Glu Gln Leu Leu Ala Leu Ser Ser Pro Ile Tyr Arg Leu Glu
        275                 280                 285 ctg gcg atg gtc ggg cga ctg ttt gct cag gat ccg cag ctt tat gcc    912
Leu Ala Met Val Gly Arg Leu Phe Ala Gln Asp Pro Gln Leu Tyr Ala
    290                 295                 300 gac atc att atg tcg tca gag cgt aat ctg gcg tta atc aaa cgt tac    960
Asp Ile Ile Met Ser Ser Glu Arg Asn Leu Ala Leu Ile Lys Arg Tyr
305                 310                 315                 320 tat aag cgt ttc ggc gag gcg att gag ttg ctg gag cag ggc gat aag   1008
Tyr Lys Arg Phe Gly Glu Ala Ile Glu Leu Leu Glu Gln Gly Asp Lys
                325                 330                 335 cag gcg ttt att gac agt ttc cgc aag gtg gag cac tgg ttc ggc gat   1056
Gln Ala Phe Ile Asp Ser Phe Arg Lys Val Glu His Trp Phe Gly Asp
            340                 345                 350 tac gca cag cgt ttt cag agt gaa agc cgc gtg tta ttg cgt cag gcg   1104
Tyr Ala Gln Arg Phe Gln Ser Glu Ser Arg Val Leu Leu Arg Gln Ala
        355                 360                 365 aat gac aat cgc cag taa                                            1122
Asn Asp Asn Arg Gln
    370
```

<210> SEQ ID NO 19
<211> LENGTH: 373
<212> TYPE: PRT
<213> ORGANISM: Escherichia coli

<400> SEQUENCE: 19

```
Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95
```

```
Ser Leu Arg Pro Val Val Ile Val Gly Gly Gly Gln Met Gly Arg
        100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
        130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
                180                 185                 190

Val Leu Gly Leu His Pro Met Phe Gly Pro Asp Ser Gly Ser Leu Ala
            195                 200                 205

Lys Gln Val Val Trp Cys Asp Gly Arg Lys Pro Glu Ala Tyr Gln
        210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
        290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

Tyr Ala Gln Arg Phe Gln Ser Glu Ser Arg Val Leu Leu Arg Gln Ala
        355                 360                 365

Asn Asp Asn Arg Gln
        370

<210> SEQ ID NO 20
<211> LENGTH: 1152
<212> TYPE: DNA
<213> ORGANISM: Erwinia herbicola
<220> FEATURE:
<221> NAME/KEY: CDS
<222> LOCATION: (1)..(1119)

<400> SEQUENCE: 20 atg gtg gct gaa ctg acc gcg tta cgc gat caa att gac agt gta gat    48
Met Val Ala Glu Leu Thr Ala Leu Arg Asp Gln Ile Asp Ser Val Asp
1               5                   10                  15 aaa gcg ctg ctg gat ctg ctg gct aag cga ctg gaa ctg gtg gcc gag    96
Lys Ala Leu Leu Asp Leu Leu Ala Lys Arg Leu Glu Leu Val Ala Glu
            20                  25                  30 gta ggt gag gtg aag agc cgt tac ggc ctg cct atc tat gtg cct gag   144
Val Gly Glu Val Lys Ser Arg Tyr Gly Leu Pro Ile Tyr Val Pro Glu
        35                  40                  45 cgt gag gcg tcg atg ctg gct tcg cgt cgc aaa gag gcc gaa gcg ctc   192
```

```
                Arg Glu Ala Ser Met Leu Ala Ser Arg Arg Lys Glu Ala Ala Leu
                 50                  55                  60 ggc gta cca ccg gat ctg att gag gat gtg ctg cgt cgc gtg atg cgg       240
Gly Val Pro Pro Asp Leu Ile Glu Asp Val Leu Arg Arg Val Met Arg
 65                  70                  75                  80 gaa tcc tat acc agc gag aat gat aaa ggc ttt aaa acc ctc tgt cct       288
Glu Ser Tyr Thr Ser Glu Asn Asp Lys Gly Phe Lys Thr Leu Cys Pro
                 85                  90                  95 gaa ctg cgc ccg gtg gtg att gtc ggt ggt aag ggc cag atg ggc cgg       336
Glu Leu Arg Pro Val Val Ile Val Gly Gly Lys Gly Gln Met Gly Arg
                100                 105                 110 ctg ttt gaa aaa atg ctc ggg cta tca ggc tac acg gtt aaa acg ctg       384
Leu Phe Glu Lys Met Leu Gly Leu Ser Gly Tyr Thr Val Lys Thr Leu
                115                 120                 125 gat aaa gag gac tgg cct cag gct gag act ctg ctc agc gat gcc gga       432
Asp Lys Glu Asp Trp Pro Gln Ala Glu Thr Leu Leu Ser Asp Ala Gly
130                 135                 140 atg gtg atc att agc gtg ccg att cac ctg acc gag cag gtg att gcc       480
Met Val Ile Ile Ser Val Pro Ile His Leu Thr Glu Gln Val Ile Ala
145                 150                 155                 160 caa ctg cca cca ctg ccg gaa gat tgt att ctg gtc gat ctg gcg tca       528
Gln Leu Pro Pro Leu Pro Glu Asp Cys Ile Leu Val Asp Leu Ala Ser
                165                 170                 175 gtc aaa aac cgg cct ctg cag gca atg ctg gct gcc cat aac ggg cct       576
Val Lys Asn Arg Pro Leu Gln Ala Met Leu Ala Ala His Asn Gly Pro
                180                 185                 190 gta ctg ggt ctg cat ccg atg ttt ggc ccg gac agc ggc agc ctg gca       624
Val Leu Gly Leu His Pro Met Phe Gly Pro Asp Ser Gly Ser Leu Ala
                195                 200                 205 aaa cag gtg gtg gtc tgg tgt gat gga aga caa ccg gaa gcg tat cag       672
Lys Gln Val Val Val Trp Cys Asp Gly Arg Gln Pro Glu Ala Tyr Gln
210                 215                 220 tgg ttc ctg gag cag att cag gtc tgg ggt gcg cgt ctg cat cgt atc       720
Trp Phe Leu Glu Gln Ile Gln Val Trp Gly Ala Arg Leu His Arg Ile
225                 230                 235                 240 agc gct gtt gag cat gac cag aac atg gca ttc att cag gcg ctg cgt       768
Ser Ala Val Glu His Asp Gln Asn Met Ala Phe Ile Gln Ala Leu Arg
                245                 250                 255 cac ttt gct acc ttc gct tat ggt ctg cat tta gcc gaa gag aac gtc       816
His Phe Ala Thr Phe Ala Tyr Gly Leu His Leu Ala Glu Glu Asn Val
                260                 265                 270 aat ctg gat cag ctg ctg gcg ctc tcg tcg ccc att tac cgg ctt gaa       864
Asn Leu Asp Gln Leu Leu Ala Leu Ser Ser Pro Ile Tyr Arg Leu Glu
                275                 280                 285 ctg gcg atg gtg ggg cgg ttg ttc gct cag gat ccg caa ctc tat gcg       912
Leu Ala Met Val Gly Arg Leu Phe Ala Gln Asp Pro Gln Leu Tyr Ala
290                 295                 300 gat atc atc atg tct tca gag agt aat ctg gcg ctg ata aaa cgc tat       960
Asp Ile Ile Met Ser Ser Glu Ser Asn Leu Ala Leu Ile Lys Arg Tyr
305                 310                 315                 320 tac cag cgg ttt ggt gaa gcg att gcg ctg ctg gag cag ggc gac aag      1008
Tyr Gln Arg Phe Gly Glu Ala Ile Ala Leu Leu Glu Gln Gly Asp Lys
                325                 330                 335 cag gcg ttt atc gcc agc ttt aac cgg gtt gaa cag tgg ttt ggc gat      1056
Gln Ala Phe Ile Ala Ser Phe Asn Arg Val Glu Gln Trp Phe Gly Asp
                340                 345                 350 cac gca aaa cgc ttc ctg gtc gaa agc cga agc ctg ttg cga tcg gcc      1104
His Ala Lys Arg Phe Leu Val Glu Ser Arg Ser Leu Leu Arg Ser Ala
                355                 360                 365
```

```
aat gac agc cgc cca taaaaaaaag gcatccagtt ggatgccttt ttt         1152
Asn Asp Ser Arg Pro
    370
```

<210> SEQ ID NO 21
<211> LENGTH: 373
<212> TYPE: PRT
<213> ORGANISM: Erwinia herbicola

<400> SEQUENCE: 21

```
Met Val Ala Glu Leu Thr Ala Leu Arg Asp Gln Ile Asp Ser Val Asp
1               5                   10                  15

Lys Ala Leu Leu Asp Leu Leu Ala Lys Arg Leu Glu Leu Val Ala Glu
                20                  25                  30

Val Gly Glu Val Lys Ser Arg Tyr Gly Leu Pro Ile Tyr Val Pro Glu
            35                  40                  45

Arg Glu Ala Ser Met Leu Ala Ser Arg Lys Glu Ala Glu Ala Leu
        50                  55                  60

Gly Val Pro Pro Asp Leu Ile Glu Asp Val Leu Arg Arg Val Met Arg
65                  70                  75                  80

Glu Ser Tyr Thr Ser Glu Asn Asp Lys Gly Phe Lys Thr Leu Cys Pro
                85                  90                  95

Glu Leu Arg Pro Val Val Ile Val Gly Gly Lys Gly Gln Met Gly Arg
            100                 105                 110

Leu Phe Glu Lys Met Leu Gly Leu Ser Gly Tyr Thr Val Lys Thr Leu
        115                 120                 125

Asp Lys Glu Asp Trp Pro Gln Ala Glu Thr Leu Leu Ser Asp Ala Gly
    130                 135                 140

Met Val Ile Ile Ser Val Pro Ile His Leu Thr Glu Gln Val Ile Ala
145                 150                 155                 160

Gln Leu Pro Pro Leu Pro Glu Asp Cys Ile Leu Val Asp Leu Ala Ser
                165                 170                 175

Val Lys Asn Arg Pro Leu Gln Ala Met Leu Ala Ala His Asn Gly Pro
            180                 185                 190

Val Leu Gly Leu His Pro Met Phe Gly Pro Asp Ser Gly Ser Leu Ala
        195                 200                 205

Lys Gln Val Val Trp Cys Asp Gly Arg Gln Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Asn Leu Asp Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Ser Asn Leu Ala Leu Ile Lys Arg Tyr
305                 310                 315                 320

Tyr Gln Arg Phe Gly Glu Ala Ile Ala Leu Leu Glu Gln Gly Asp Lys
                325                 330                 335

Gln Ala Phe Ile Ala Ser Phe Asn Arg Val Glu Gln Trp Phe Gly Asp
            340                 345                 350

His Ala Lys Arg Phe Leu Val Glu Ser Arg Ser Leu Leu Arg Ser Ala
```

Asn Asp Ser Arg Pro
    370

<210> SEQ ID NO 22
<211> LENGTH: 1129
<212> TYPE: DNA
<213> ORGANISM: Lycopersicon esculentum

<400> SEQUENCE: 22

| | | | | | |
|---|---|---|---|---|---|
| atgttttccc | tttcatctat | acaatctaac | aatattcaat | ctcaatcatc | ttcgtcgcta | 60 |
| ctcttcaatc | atcatcacca | gcattcaact | atttcaactc | ggtttcatca | ccaccgccta | 120 |
| ctcttccctc | tccgtgccca | aaatagcgac | ttaactacag | ccaccaccaa | taacaactat | 180 |
| gtcgatcttg | atgacaatct | aaccagactt | gataaatttt | caaaatcatt | aagtatttcg | 240 |
| aatatcgaag | aaaatacatc | attaaatccc | ctcttatgtt | ccaataacaa | gctcaaaata | 300 |
| gctatcatag | gctttggaaa | ctttggacaa | tttattgcca | atcctttat | caaacaaggc | 360 |
| catgttgtat | tagctcattc | acgtagtgat | tattccctca | tagcacaatc | ccttaatgtc | 420 |
| cacttctttc | aagatcctaa | tgacttatgt | gaacaacatc | ctgacgttat | tttactttgc | 480 |
| acatccatca | attcactcga | aaacgtcatt | cgttcccttc | ccatccaaaa | gcttaaacgt | 540 |
| aacacacttt | tcgtagacgt | attatcagtc | aaagaattcc | cgaaaaacat | ttttcttcaa | 600 |
| tcactaccaa | agaatttga | tattttgtgt | actcatccta | tgtttggtcc | aacaagtggt | 660 |
| aaagacaatt | ggaaaggact | accatttatg | tatgacaaag | ttagaattgg | acaagaagag | 720 |
| tcaagaatta | aaagagtcaa | caatttatc | aacattttg | taaaagaagg | ttgtagaatg | 780 |
| gttgaaatga | gttgtagtga | acatgacaag | tatgctgctg | gatcacaatt | tattacacat | 840 |
| actattggaa | gaatgttaca | aagacttggg | acacaaacaa | ctcctataaa | cacaaaagga | 900 |
| tatgaaagtt | tgttgaattt | gatggagaat | acaactagtg | atagttttga | tttgtattgt | 960 |
| ggtttgctta | tgtataacaa | taattcaatg | gaggtgttag | agaaactaga | tgcagcattg | 1020 |
| gatagtttga | aagggaatt | atttggacaa | gttcttcaaa | agttggagaa | agagtggaa | 1080 |
| aagggaagta | agttagcttt | acctactcct | gattttagta | agaaaattg | | 1129 |

<210> SEQ ID NO 23
<211> LENGTH: 32
<212> TYPE: DNA
<213> ORGANISM: Artificial
<220> FEATURE:
<223> OTHER INFORMATION: Oligonucleotide P1

<400> SEQUENCE: 23
tctccatatg atctttcaat ctcattctca tc                     32

<210> SEQ ID NO 24
<211> LENGTH: 32
<212> TYPE: DNA
<213> ORGANISM: Artificial
<220> FEATURE:
<223> OTHER INFORMATION: Oligonucleotide P2

<400> SEQUENCE: 24
ctaactaact aactacatac ctcatcatat cc                     32

<210> SEQ ID NO 25
<211> LENGTH: 26
<212> TYPE: DNA

```
<213> ORGANISM: Artificial
<220> FEATURE:
<223> OTHER INFORMATION: Oligonucleotide P3

<400> SEQUENCE: 25
cctctctttc catatgctcc cttctc                                        26

<210> SEQ ID NO 26
<211> LENGTH: 33
<212> TYPE: DNA
<213> ORGANISM: Artificial
<220> FEATURE:
<223> OTHER INFORMATION: Oligonucleotide P4

<400> SEQUENCE: 26
ccgccagcca cctccatatg accgacacca tcc                                33

<210> SEQ ID NO 27
<211> LENGTH: 25
<212> TYPE: DNA
<213> ORGANISM: Artificial
<220> FEATURE:
<223> OTHER INFORMATION: Oligonucleotide P5

<400> SEQUENCE: 27
cgccacccct catatgcgta tcgcc                                         25

<210> SEQ ID NO 28
<211> LENGTH: 34
<212> TYPE: DNA
<213> ORGANISM: Artificial
<220> FEATURE:
<223> OTHER INFORMATION: Oligonucleotide P6

<400> SEQUENCE: 28
gatgcatctt tgcatatgat gaggtcagaa gatg                               34

<210> SEQ ID NO 29
<211> LENGTH: 35
<212> TYPE: DNA
<213> ORGANISM: Artificial
<220> FEATURE:
<223> OTHER INFORMATION: Oligonucleotide P7

<400> SEQUENCE: 29
cagtataatt agtagtcaag gatcctgact gagag                              35

<210> SEQ ID NO 30
<211> LENGTH: 31
<212> TYPE: DNA
<213> ORGANISM: Artificial
<220> FEATURE:
<223> OTHER INFORMATION: Oligonucleotide P8

<400> SEQUENCE: 30
gctaaaactc ttctccttca atacttacct g                                  31
```

METHODS FOR IDENTIFYING HERBICIDAL COMPOUNDS

RELATED APPLICATIONS

This application is a national stage application (under 35 U.S.C. 371) of PCT/FRO1/03832 filed Dec. 5, 2001, which claims the benefit of French application 00/15,723 filed Dec. 5, 2000.

The contents of the following submission on compact discs are incorporated herein by reference in its entirety: two copies of the Sequence Listing (REPLACEMENT COPY 1 and COPY 2) and a computer readable form copy of the Sequence Listing (REPLACEMENT CRF COPY), all on compact disc, each containing: file name: 5500-120 Sequence Listing; date recorded: Oct. 16, 2006; size 93 KB.

The present invention relates to novel enzymes having arogenate dehydrogenase activity, in particular plant arogenate dehydrogenase enzymes, and also to the genes encoding these enzymes. The arogenate hydrogenase enzymes according to the invention catalyze the final step in the metabolic pathway of tyrosine biosynthesis and, in this respect, constitute potential targets for herbicides. The present invention therefore also relates to a method for identifying herbicidal compounds having these enzymes as a target, said herbicidal compounds preventing tyrosine biosynthesis by attaching to said enzymes. The invention also relates to transgenic plants tolerant to herbicidal compounds having as a target an enzyme involved in the biosynthetic pathway for tyrosine, in particular an enzyme involved in the conversion of prephenate to L-tyrosine, in particular an arogenate dehydrogenase enzyme. These plants become tolerant by expression, in their tissues, of a prephenate dehydrogenase enzyme, this enzyme being insensitive to said herbicidal compounds and enabling the plant to synthesize tyrosine despite treatment with said herbicidal compounds.

The biosynthetic pathway for aromatic amino acids constitutes a metabolic pathway which is essential for plants, bacteria and fungi. In addition to the biosynthesis of tyrosine, phenylalanine and tryptophan, this metabolic pathway plays an essential role in the production of many secondary aromatic metabolites involved in processes such as plant-microbe interactions, the biosynthesis of structural biopolymers such as lignin and suberin, hormone synthesis, or quinone synthesis. Among all the living organisms which have this metabolic pathway, two pathways have been identified for converting prephenate to tyrosine (FIG. 1; Stenmark et al., 1974). In most chlorophyll-containing bacteria, some microorganisms and most plants, L-tyrosine is synthesized via the arogenate pathway (Abou-Zeid et al., 1995; Byng et al., 1981; Connely and Conn 1986; Frazel and Jensen 1979; Gaines et al., 1982; Hall et al., 1982; Keller et al., 1985; Mayer et al., 1985). In this pathway, the prephenate is transaminated to arogenate by a specific transaminase, prephenate aminotransferase (EC 2.6.1.57), and the arogenate is then converted to L-tyrosine by an arogenate dehydrogenase (EC 1.3.1.43; ADH on FIG. 1). In a different manner, in organisms such as the bacterium *Escherichia coli* or yeast, the prephenate is, initially, converted to p-hydroxyphenylpyruvate by a prephenate dehydrogenase (EC 1.3.1.12, EC 1.3.1.13), which p-hydroxyphenylpyruvate is transaminated to L-tyrosine (Lingens et al., 1967). By virtue of its role in the biosynthetic pathway for tyrosine in plants, the arogenate dehydrogenase enzyme constitutes a potential target for novel herbicides.

Other enzymes involved in this metabolic pathway already constitute major herbicide targets. Mention may, for example, be made of the enzyme 5-enolpyruvyl-shikimate 3-phosphate synthase (EPSPS), involved upstream of prephenate synthesis, which is the target for the total herbicide glyphosate. Mention may also be made of the enzyme p-hydroxyphenylpyruvate dioxygenase (HPPD) involved in the conversion of p-hydroxyphenylpyruvate to homogentisate. HPPD is the target for novel families of herbicides, the activity of which leads to bleaching of the leaves (Schulz et al., 1993; Secor 1994). These herbicides are in particular isoxazoles (EP 418 175, EP 470 856, EP 487 352, EP 527 036, EP 560 482, EP 682 659, U.S. Pat. No. 5,424,276), in particular isoxaflutole, a maize-selective herbicide, diketonitriles (EP 496 630, EP 496 631) in particular 2-cyano-3-cyclopropyl-1-(2-SO$_2$CH$_3$-4-CF$_3$ phenyl)propane-1,3-dione and 2-cyano-3-cyclopropyl-1-(2-SO$_2$CH$_3$-4,2,3-Cl$_2$ phenyl) propane-1,3-dione, triketones (EP 625 505, EP 625 508, U.S. Pat. No. 5,506,195), in particular sulcotrione or mesotrione, or else pyrazolinates.

One of the advantages of the herbicides having for a target enzymes involved in the metabolic pathways essential to plants is their broad spectrum of activity on plants of distant phylogenetic origins. However, such herbicides also have the major drawback, when they are applied to crops in order to eliminate the undesirable plants or "weeds", of also acting on the cultivated plants. This drawback can be overcome by using cultivated plants tolerant to said herbicides. Such plants are generally obtained by genetic engineering, by introducing into their genome a gene encoding an enzyme for resistance to said herbicide, in such a way that they overexpress said enzyme in their tissues. To date, three main strategies using genetic engineering have been employed to make plants tolerant to herbicides. The first consists in detoxifying the herbicide by transforming the plant with a gene encoding a detoxification enzyme. This enzyme converts the herbicide, or its active metabolite, to nontoxic degradation products, such as, for example, the enzymes for tolerance to bromoxynil or to basta (EP 242 236, EP 337 899). The second strategy consists in transforming the plant with a gene encoding the target enzyme mutated in such a way that it is less sensitive to the herbicide, or its active metabolite, such as, for example, the enzymes for tolerance to glyphosate (EP 293 356, Padgette S. R. & al., J. Biol. Chem., 266, 33, 1991). The third strategy consists in overexpressing the sensitive target enzyme so as to produce, in the plant, large amounts of target enzyme, if possible much greater than the amount of herbicide entering the plant. This strategy, which has been used to successfully obtain plants tolerant to HPPD inhibitors (WO 96/38567), makes it possible to maintain a sufficient level of functional enzyme despite the presence of its inhibitor.

The fact that two biosynthetic pathways for L-tyrosine exist in different taxonomic groups, and in particular that the pathway directly converting prephenate to p-hydroxyphenylpyruvate is not found in plants, makes it possible to envision a fourth strategy for making plants tolerant to herbicides. Specifically, in the case of use of a herbicidal compound having as target the arogenate dehydrogenase enzyme in plants, transforming the plants intended to be made tolerant with a gene encoding a bacterial or yeast prephenate dehydrogenase enzyme will enable said plants to synthesize L-tyrosine, and therefore to tolerate the presence of the herbicidal compound despite the inhibition of the arogenate dehydrogenase enzyme by said herbicidal compound. This novel strategy therefore consists in creating, in the plants intended to be made resistant, a bypassing of the natural metabolic pathway for tyrosine biosynthesis, which pathway uses the arogenate dehydrogenase enzyme, by artificial implantation in these plants of a novel metabolic pathway for tyrosine biosynthesis, which uses the prephenate dehydrogenase enzyme. Such bypassing allows the plants possessing it, preferably plants of agronomic interest, to tolerate the presence of the herbicidal compound which inhibits the natural metabolic pathway, whereas the plants not possessing this bypassing, in particular the weeds, will be sensitive to said herbicidal compound.

DESCRIPTION

The present invention therefore relates to novel isolated polynucleotides encoding an enzyme having arogenate dehydrogenase activity. According to the present invention, the term "polynucleotide" is intended to mean a natural or artificial nucleotide sequence which may be of the DNA or RNA type, preferably of the DNA type, in particular double-stranded. The expression "enzymes having arogenate dehydrogenase activity" is intended to mean the enzymes capable of converting arogenate to L-tyrosine. The arogenate dehydrogenase activity is measured by any method which makes it possible either to measure a decrease in the amount of the arogenate substrate, or to measure an accumulation of a product derived from the enzyme reaction, namely L-tyrosine or the cofactor NADPH. In particular, the arogenate dehydrogenase activity can be measured by the method described in example 4.

According to a particular embodiment of the invention, the polynucleotides encoding an arogenate dehydrogenase enzyme comprise polynucleotides encoding the polypeptide sequence selected from the sequence described in the sequence identifier SEQ ID NO: 3, SEQ ID NO: 5, SEQ ID NO: 7, SEQ ID NO: 9, SEQ ID NO: 11 or SEQ ID NO: 13. It is well known to those skilled in the art that this definition includes all the polynucleotides which, although comprising nucleotide sequences which are different as a result of the degeneracy of the genetic code, encode the same amino acid sequence, which sequence is represented by the sequence identifiers SEQ ID NO: 3, SEQ ID NO: 5, SEQ ID NO: 7, SEQ ID NO: 9, SEQ ID NO: 11 or SEQ ID NO: 13.

The present invention also comprises isolated polynucleotides encoding arogenate dehydrogenase enzymes and capable of hybridizing selectively to one of the polynucleotides described above, or a fragment of these polynucleotides constituting a probe. According to the invention, the expression "polynucleotide capable of hybridizing selectively" is intended to mean the polynucleotides which, by one of the usual methods of the state of the art (Sambrook et al., 1989, Molecular Cloning: A Laboratory Manual, Nolan C. ed., New York: Cold Spring Harbor Laboratory Press), hybridize with the polynucleotides above, or with the probes which are derived therefrom, at a level significantly greater than the background noise. The background noise may be associated with the hybridization of other polynucleotides present, for example other cDNAs present in a cDNA library. The level of the signal generated by the interaction between the polynucleotide capable of hybridizing selectively and the polynucleotides defined by the sequences SEQ ID NOS: above according to the invention, or the probes, is generally 10 times, preferably 100 times, more intense than that generated by the interaction with other DNA sequences generating the background noise. The level of interaction can be measured, for example, by labeling the polynucleotides described above or the probes with radioactive elements, such as $^{32}P$. Selective hybridization is generally obtained using very severe conditions for the medium (for example 0.03 M NaCl and 0.03 M sodium citrate at approximately 50° C.-60° C.).

The invention also comprises isolated polynucleotides encoding arogenate dehydrogenase enzymes, and homologs of the polynucleotides described above. According to the invention, the term "homolog" is intended to mean polynucleotides exhibiting one or more sequence modifications compared to the nucleotide sequences described above and encoding an enzyme with functional arogenate dehydrogenase activity. These modifications may be natural or obtained artificially according to the usual techniques of mutation leading in particular to the addition, deletion or substitution of one or more nucleotides compared to the sequences of the invention. These modifications determine a degree of homology with respect to the sequences described above. Advantageously, the degree of homology will be at least 70% compared to the sequences described, preferably at least 80%, more preferentially at least 90%. The methods for measuring and identifying homologies between nucleic acid sequences are well known to those skilled in the art. Use may, for example, be made of the PILEUP or BLAST programs (Basic Local Alignment Search Tool; Altschul et al., 1993, J. Mol. Evol. 36: 290-300; Altschul et al., 1990, J. Mol. Biol. 215: 403-10; see also http://www.ncbi.nlm.nih.gov/BLAST/).

The present invention also relates to fragments of the polynucleotides described above. The term "fragment" denotes in particular a fragment of at least 20 nucleotides, in particular of at least 50 nucleotides, and preferably of at least 100 nucleotides.

According to a particular embodiment of the invention, the polynucleotide according to the invention is represented by the sequence identifier SEQ ID NO: 1, SEQ ID NO: 2, SEQ ID NO: 4, SEQ ID NO: 6, SEQ ID NO: 8, SEQ ID NO: 10 or SEQ ID NO: 12.

The present invention also relates to polynucleotides comprising at least one of the polynucleotides as described above.

All the polynucleotides described above encode arogenate dehydrogenase enzymes. Consequently, the invention therefore extends to all the arogenate dehydrogenase enzymes encoded by all of these polynucleotides.

BRIEF DESCRIPTION OF THE DRAWINGS

FIG. 3 shows a table of enzymatic activity of TyrA-ATc, TyrA-AT1 and TyrA-AT2.

FIG. 4 shows a table of *Synechocystis* arogenate dehydrogenase enzymatic activity.

Figure 1:
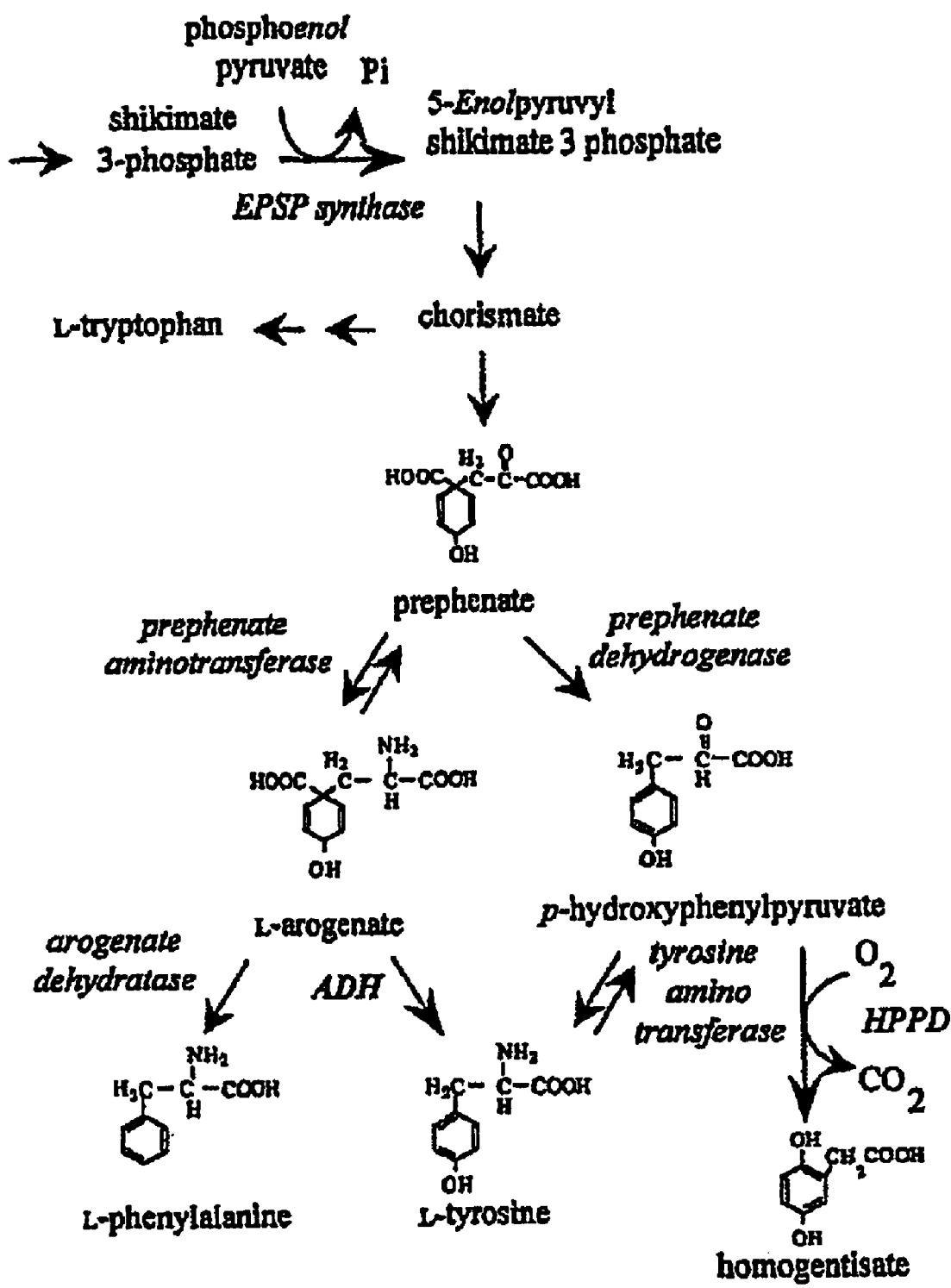
FIG. 1 shows a schematic of the arogenate pathway.

According to a particular embodiment of the invention, the arogenate dehydrogenase enzyme is an enzyme the peptide sequence of which is selected from the sequence described by the sequence identifier SEQ ID NO: 3, SEQ ID NO: 5, SEQ ID NO: 7, SEQ ID NO: 9, SEQ ID NO: 11 or SEQ ID NO: 13., or a fragment of these sequences. The term "fragment" is intended to mean essentially a biologically active fragment, i.e. a fragment of the sequence of an arogenate dehydrogenase enzyme having the same activity as a complete arogenate dehydrogenase enzyme.

According to a particular embodiment of the invention, the polynucleotides and the arogenate dehydrogenase enzymes described above originate from plants. More particularly, they originate from plants of the *Arabidopsis* genus, preferably of the *A. thaliana* genus, or from plants of the Picea genus, preferably Picea glauca.

According to another particular embodiment of the invention, the polynucleotides and the arogenate dehydrogenase enzymes described above originate from bacteria. More particularly, they originate from bacteria of the *Synechocystis* genus.

The present invention also relates to a chimeric gene comprising, functionally linked to one another, at least one promoter which is functional in a host organism, a polynucleotide encoding an arogenate dehydrogenase enzyme as defined in the present invention, and a terminator element which is functional in this same host organism. The various elements that a chimeric gene may contain are, firstly, elements which regulate the transcription, translation and maturation of proteins, such as a promoter, a sequence encoding a signal peptide or a transit peptide, or a terminator element constituting a polyadenylation signal and, secondly, a polynucleotide encoding a protein. The expression "functionally linked to one another" means that said elements of the chimeric gene are linked to one another in such a way that the functioning of one of these elements is affected by that of another. By way of example, a promoter is functionally linked to a coding sequence when it is capable of affecting the expression of said coding sequence. The construction of the chimeric gene according to the invention and the assembly of its various elements can be carried out using techniques well known to those skilled in the art, in particular those described by Sambrook et al., (1989, Molecular Cloning: A Laboratory Manual, Nolan C. ed., New York: Cold Spring Harbor Laboratory Press). The choice of the regulatory elements constituting the chimeric gene depends essentially on the host species in which they must function, and those skilled in the art are capable of selecting regulatory elements which are functional in a given host organism. The term "functional" is intended to mean capable of functioning in a given host organism.

The promoters which the chimeric gene according to the invention can contain are either constitutive or inducible. A constitutive promoter according to the present invention is a promoter which induces the expression of a coding sequence in all the tissues of a host organism and continuously, i.e. throughout the duration of the life cycle of said organism. Some of these promoters may be tissue-specific, i.e. express the coding sequence continuously, but only in a particular tissue of the host organism. Constitutive promoters may originate from any type of organism. Among the constitutive promoters which can be used in the chimeric gene of the present invention, mention may, for example, be made of bacterial promoters, such as that of the octopine synthase gene or that of the nopaline synthase gene, of viral promoters, such as that of the gene controlling transcription of the 19S or 35S RNAs of the cauliflower mosaic virus (Odell et al., 1985, Nature, 313, 810-812), or the promoters of the cassava vein mosaic virus (as described in patent application WO 97/48819). Among the promoters of plant origin, mention will be made of the promoter of the ribulose-biscarboxylase/oxygenase (RuBisCO) small sub-unit gene, the promoter of a histone gene as described in application EP 0 507 698, or the promoter of a rice actin gene (U.S. Pat. No. 5,641,876).

According to another particular embodiment of the invention, the chimeric gene contains an inducible promoter. An inducible promoter is a promoter which only functions, i.e. which only induces expression of a coding sequence, when it is itself induced by an inducing agent. This inducing agent is generally a substance which can be synthesized in the host organism subsequent to a stimulus external to said organism, this external stimulus possibly being, for example, a pathogenic agent. The inducing agent may also be a substance external to this host organism, capable of penetrating into this host organism. Advantageously, the promoter used in the present invention is inducible subsequent to an attack on the host organism by a pathogenic agent. Such promoters are known, such as, for example, the promoter of the plant O-methyl-transferase class II (COMT II) gene described in patent application FR 99 03700, the *Arabidopsis* PR-1 promoter (Lebel et al., 1998, Plant J. 16(2):223-233), the EAS4 promoter of the tobacco sesquiterpene synthase gene (Yin et al., 1997, Plant Physiol. 115(2): 437-451), or the promoter of the gene encoding 3-hydroxy-3-methyl-glutaryl coenzyme A reductase (Nelson et al., 1994, Plant Mol. Biol. 25(3): 401-412).

Among the terminator elements which may be used in the chimeric gene of the present invention, mention may, for example, be made of the nos terminator element of the gene encoding *Agrobacterium tumefaciens* nopaline synthase (Beven et al., 1983, Nucleic Acids Res. 11(2), 369-385), or the terminator element of a histone gene as described in application EP 0 633 317.

It also appears to be important for the chimeric gene to additionally comprise a signal peptide or a transit peptide which makes it possible to control and orient the production of the arogenate dehydrogenase enzyme specifically in a part of the host organism, such as, for example, the cytoplasm, a particular compartment of the cytoplasm, or the cell membrane or, in the case of plants, in a particular type of cellular compartment, for example the chloroplasts, or in the extracellular matrix.

The transit peptides can be either single or double. The double transit peptides are optionally separated by an intermediate sequence, i.e. they comprise, in the direction of transcription, a sequence encoding a transit peptide of a plant gene encoding an enzyme located in plastids, a portion of sequence of the mature N-terminal portion of a plant gene encoding an enzyme located in plastids, and then a sequence encoding a second transit peptide of a plant gene encoding an enzyme located in plastids. Such double transit peptides are, for example, described in patent application EP 0 508 909.

Signal peptides of use according to the invention which may be mentioned include in particular the signal peptide of the tobacco PR-1α gene described by Cornelissen et al. (1987, Nucleic Acid Res. 15, 6799-6811), in particular when the chimeric gene according to the invention is introduced into plant cells or plants, or the signal peptide of the Mat α1 factor precursor (Brake et al., 1985, In: Gething M.-J. (eds.); Protein transport and secretion, pp. 103-108, Cold Spring Harbor Laboratory Press, New York), when the chimeric gene according to the invention is introduced into yeast.

The present invention also relates to a vector containing a chimeric gene according to the invention. The vector according to the invention is of use for transforming a host organism and expressing an arogenate dehydrogenase enzyme in this host organism. This vector may be a plasmid, a cosmid, a bacteriophage or a virus. In general, the main qualities of this vector should be an ability to persist and to self-replicate in the host organism's cells, in particular by virtue of the presence of an origin of replication, and to express therein an arogenate dehydrogenase enzyme. The choice of such a vector and also the techniques for inserting the chimeric gene according to the invention therein are widely described in Sambrook et al. (1989, Molecular Cloning: A Laboratory Manual, Nolan C. ed., New York:

Cold Spring Harbor Laboratory Press) and are part of the general knowledge of those skilled in the art. Advantageously, the vector used in the present invention also contains, in addition to the chimeric gene of the invention, a gene encoding a selectable marker. This selectable marker makes it possible to select the host organisms effectively transformed, i.e. those having incorporated the vector. According to a particular embodiment of the invention, the host organism to be transformed is a microorganism, in particular a yeast, a bacterium, a fungus or a virus. According to another embodiment, the host organism is a plant or a plant cell. Among the genes encoding selectable markers which can be used, mention may be made of genes for resistance to antibiotics, such as, for example, the hygromycin phosphotransferase (Gritz et al., 1983, Gene 25: 179-188), but also the genes for tolerance to herbicides, such as the bar gene (White et al., NAR 18: 1062, 1990) for tolerance to bialaphos, the EPSPS gene (U.S. Pat. No. 5,188,642) for tolerance to glyphosate or else the HPPD gene (WO 96/38567) for tolerance to isoxazoles. Mention may also be made of genes encoding readily identifiable enzymes such as the GUS enzyme, or genes encoding pigments or enzymes which regulate the production of pigments in the transformed cells. Such selectable marker genes are in particular described in patent applications WO 91/02071, WO 95/06128, WO 96/38567 and WO 97/04103.

The present invention also relates to transformed host organisms containing a vector as described above. The term "host organism" is intended to mean any lower or higher monocellular or pluricellular organism into which the chimeric gene according to the invention can be introduced, so as to produce arogenate dehydrogenase enzyme. They are in particular bacteria, for example *Escherichia coli*, yeast, in particular of the *Saccharomyces, Kluyveromyces* or *Pichia* genera, fungi, in particular *Aspergillus*, a baculovirus, or preferably plant cells and plants.

According to the invention, the term "plant cell" is intended to mean any cell derived from a plant and able to constitute undifferentiated tissues such as calluses, differentiated tissues such as embryos, parts of plants, plants or seeds.

According to the invention, the term "plant" is intended to mean any differentiated multicellular organism capable of photosynthesis, in particular monocotyledons or dicotyledons.

The term "transformed host organism" is intended to mean a host organism which has incorporated into its genome the chimeric gene of the invention and consequently produces an arogenate dehydrogenase enzyme in its tissues, or in a culture medium. Those skilled in the art can use one of the many known methods of transformation to obtain the host organisms according to the invention.

One of these methods consists in bringing the cells to be transformed into contact with polyethylene glycol (PEG) and the vectors of the invention (Chang and Cohen, 1979, Mol. Gen. Genet. 168(1), 111-115); Mercenier and Chassy, 1988, Biochimie 70(4), 503-517). Electroporation is another method, which consists in subjecting the cells or tissues to be transformed and the vectors of the invention to an electric field (Andreason and Evans, 1988, Biotechniques 6(7), 650-660; Shigekawa and Dower, 1989, Aust. J. Biotechnol. 3(1), 56-62). Another method consists in directly injecting the vectors into the host cells or tissues by microinjection (Gordon and Ruddle, 1985, Gene 33(2), 121-136). Advantageously, the "biolistic" method may be used. In consists in bombarding cells or tissues with particles onto which the vectors of the invention are adsorbed (Bruce et al., 1989, Proc. Natl. Acad. Sci. USA 86(24), 9692-9697; Klein et al., 1992, Biotechnology 10(3), 286-291; U.S. Pat. No. 4,945, 050). Preferentially, the plant transformation will be carried out using bacteria of the *Agrobacterium* genus, preferably by infecting the cells or tissue of said plants by *A. tumefaciens* (Knopf, 1979, Subcell. Biochem. 6, 143-173; Shaw et al., 1983, Gene 23(3): 315-330) or *A. rhizogenes* (Bevan and Chilton, 1982, Annu. Rev. Genet. 16: 357-384; Tepfer and Casse-Delbart, 1987, Microbiol. Sci. 4(1), 24-28). Preferentially, the transformation of plant cells with *Agrobacterium tumefaciens* is carried out according to the protocol described by Ishida et al. (1996, Nat. Biotechnol. 14(6), 745-750).

Those skilled in the art will choose the appropriate method as a function of the nature of the host organism to be transformed.

The present invention therefore also relates to a method for preparing the arogenate dehydrogenase enzyme, comprising the steps of culturing a transformed host organism comprising a gene encoding an arogenate dehydrogenase enzyme as defined above, in a suitable culture medium, recovering the arogenate dehydrogenase enzyme produced from the culture medium by centrifugation or by filtration, and then purifying the recovered enzyme by passing it through at least one chromatography column. These steps bring about the extraction and the purification, which may be total or partial, of the arogenate dehydrogenase enzyme obtained. Preferentially, the transformed organism is a microorganism, in particular a bacterium, a yeast, a fungus or a virus.

The present invention also comprises a method for identifying a herbicidal compound having as a target an arogenate dehydrogenase enzyme, characterized in that:
  (a) at least two samples, each containing an equivalent amount of arogenate dehydrogenase enzymes in solution, are prepared;
  (b) one of the samples is treated with a compound;
  (c) the arogenate dehydrogenase activity is measured in each one of said samples;
  (d) the compound used in step (b) is identified as being a herbicidal compound when the activity measured in step (c) is significantly less in the treated sample compared to the untreated sample;
  (e) the herbicidal activity of the compound identified in step (d) is validated by treating plants with said compound.

According to the present method, the measurement of the arogenate dehydrogenase activity is carried out by any method which makes it possible either to measure a decrease in the amount of arogenate substrate, or to measure an accumulation of a product derived from the enzyme reaction, namely L-tyrosine or the cofactor NADPH. In particular, the measurement of the arogenate dehydrogenase activity can be carried out by the method described in example 4. In addition, the herbicidal activity validated in step (e) of the present method may be a lethal activity resulting in the death of the treated plant, or an activity which significantly slows down the growth of the treated plant.

According to the invention, the term "compound" is intended to mean any chemical compound or mixture of chemical compounds, including peptides and proteins. According to the invention, the term "mixture of compounds" is understood to mean at least two different compounds, such as, for example, the (dia)stereoisomers of a molecule, mixtures of natural origin derived from the extraction of biological material (plants, plant tissues, bacterial cultures, yeast cultures or fungal cultures, insects, animal tissues, etc.) or unpurified or totally or partially purified reaction mixtures, or else mixtures of products derived from combinatorial chemistry techniques.

According to a particular embodiment of the method according to the invention, the arogenate dehydrogenase enzymes used originate from plants, preferably from *Arabidopsis thaliana*.

According to another embodiment of the method according to the invention, the arogenate dehydrogenase enzymes used originate from bacteria, preferably bacteria of the *Synechocystis* genus.

Preferably, the arogenate dehydrogenase enzymes used in the method according to the invention are the enzymes according to the present invention, in particular those represented by SEQ ID NO: 3, SEQ ID NO: 5, SEQ ID NO: 7, SEQ ID NO: 9, SEQ ID NO: 11 or SEQ ID NO: 13.

The invention also extends to the herbicidal compounds identified using the method mentioned above, in particular the herbicidal compounds having as a target an arogenate dehydrogenase enzyme, i.e. those which inhibit the activity of this enzyme. Preferentially, the herbicidal compounds are not general enzyme inhibitors. Also preferentially, the herbicidal compounds according to the invention are not compounds already known to have herbicidal activity.

The present invention also relates to herbicidal agrochemical compositions comprising, as active material, at least an effective amount of a herbicidal compound according to the invention.

According to the invention, the term "herbicidal agrochemical composition" is intended to mean a composition which can be applied preventatively or curatively to the areas on which cultivated plants are being or must be grown, in order to prevent the development of undesirable plants or "weeds" on the areas on which said cultivated plants are grown, whatever their state of development. An effective amount of herbicidal compound according to the invention corresponds to an amount of compound which makes it possible to destroy or inhibit the growth of the undesirable plants.

The herbicidal agrochemical compositions according to the invention comprise a herbicidal compound according to the invention or one of its agriculturally acceptable salts or a metal or metalloid complex of this compound, in combination with an agriculturally acceptable solid or liquid carrier and/or a surfactant, also agriculturally acceptable. In particular, the usual inert carriers and the usual surfactants can be used. These compositions cover not only the compositions ready to be applied to a plant or a seed to be treated using a suitable device, such as a spraying or dusting device, but also the concentrated commercially available compositions which must be diluted before they are applied to the crop.

The herbicidal compositions according to the invention may also contain many other ingredients, such as, for example, protective colloids, adhesives, thickeners, thixotropic agents, penetrating agents, stabilizers or sequestering agents. More generally, the active materials can be combined with any solid or liquid additives which comply with the usual formulating techniques.

According to the present invention, the term "carrier" denotes a natural or synthetic, organic or inorganic material with which the active material is combined in order to facilitate its application to the parts of the plant. This carrier is therefore generally inert and it must be agriculturally acceptable. The carrier may be solid (for example clays, natural or synthetic silicates, silica, resins, waxes, solid fertilizers) or liquid (for example water, alcohols, in particular butanol).

The surfactant may be an emulsifier, dispersing agent or wetting agent of the ionic or nonionic type, or a mixture of such surfactants. Mention may, for example, be made of polyacrylic acid salts, lignosulfonic acid salts, phenolsulfonic or naphthalenesulfonic acid salts, polycondensates of ethylene oxide with fatty alcohols or with fatty acids or with fatty amines, substituted phenols (in particular alkylphenols or arylphenols), salts of sulfosuccinic acid esters, taurine derivatives (in particular alkyl taurates), phosphoric esters of alcohols or of phenols which are polyoxyethylated, esters of fatty acids and of polyols, and derivatives of the above compounds containing sulfate, sulfonate and phosphate functions. The presence of at least one surfactant is generally essential when the active material and/or the inert carrier are not water-soluble and when the vector agent for the application is water.

The present invention also relates to transgenic plants tolerant to a herbicidal compound having as a target an enzyme involved in one of the metabolic steps of conversion of prephenate to L-tyrosine, characterized in that they contain a gene encoding a prephenate dehydrogenase enzyme and express said enzyme in their tissue. A prephenate dehydrogenase enzyme is an enzyme which catalyzes the reaction of conversion of prephenate to p-hydroxyphenylpyruvate. The identification of an enzyme with prephenate dehydrogenase activity can be carried out by any method which makes it possible either to measure a decrease in the amount of the prephenate substrate, or to measure an accumulation of a product derived from the enzyme reaction, namely p-hydroxyphenylpyruvate or one of the cofactors NADH or NADPH. In particular, the measurement of the prephenate dehydrogenase activity can be carried out using the method described in example 4.

According to a particular embodiment of the invention, the transgenic plants according to the invention are tolerant with respect to a herbicidal compound having as a target an arogenate dehydrogenase enzyme, preferably an arogenate dehydrogenase enzyme as described in the present invention.

According to another particular embodiment of the invention, the transgenic plants according to the invention are tolerant with respect to a herbicidal compound having as a target a prephenate aminotransferase enzyme.

According to a particular embodiment of the invention, the gene encoding the prephenate dehydrogenase enzyme expressed in the tolerant plants according to the invention is a yeast gene. Preferably, it is the gene encoding the *Saccharomyces cerevisiae* prephenate dehydrogenase enzyme (accession No. NC001134) as described in Mannhaupt et al. (1989, Gene 85, 303-311) and represented by the sequence identifier SEQ ID NO: 14.

According to another particular embodiment of the invention, the gene encoding the prephenate dehydrogenase enzyme expressed in the tolerant plants according to the invention is a bacterial gene. Preferably, it is a gene from a bacterium of the *Bacillus* genus, in particular of the species *B. subtilis* (accession No. M80245) as represented by the sequence identifier SEQ ID NO: 16. Preferably, it is a gene from a bacterium of the *Escherichia* genus, in particular of the species *E. coli* (accession No. M10431) as described in Hudson et al. (1984, J. Mol. Biol. 180(4), 1023-1051) and represented by the sequence identifier SEQ ID NO: 18. Preferably, it is a gene from a bacterium of the *Erwinia* genus, in particular the species *E. herbicola* (accession No. 43343) as represented by the sequence identifier SEQ ID NO: 20.

According to particular embodiment of the invention, the gene encoding the prephenate dehydrogenase enzyme expressed in the tolerant plants according to the invention is a fungal gene.

The transgenic plants according to the invention are obtained by genetic transformation with a gene encoding a prephenate dehydrogenase enzyme. Preferably, this gene is a chimeric gene comprising, functionally linked to one another, at least one promoter which is functional in a host organism, a polynucleotide encoding a prephenate dehydrogenase enzyme, and a terminator element which is functional in this same host organism. This gene is generally introduced into a vector, which is used to introduce said gene into said plants by one of the methods of transformation described above.

The present invention also relates to a method for producing plants tolerant with respect to herbicidal compounds having as a target an enzyme involved in one of the metabolic steps for conversion of prephenate to L-tyrosine, characterized in that said plants are transformed with a gene encoding a prephenate dehydrogenase enzyme in such a way that they express it in their tissues.

According to a particular embodiment of the invention, the present method applies to the production of plants tolerant with respect to a herbicidal compound having as a target an arogenate dehydrogenase enzyme as described in the present invention.

According to another particular embodiment of the invention, the present method applies to the production of plants tolerant with respect to a herbicidal compound having as a target a prephenate aminotransferase enzyme.

The present method therefore also comprises a method for producing plants tolerant with respect to a herbicidal compound having as a target an arogenate dehydrogenase enzyme, characterized in that said plants are transformed with a gene encoding a prephenate dehydrogenase enzyme in such a way that they express it in their tissues.

The transgenic plants according to the invention may also contain, in addition to a gene encoding a prephenate dehydrogenase enzyme, at least one other gene containing a polynucleotide encoding a protein of interest. Among these polynucleotides encoding a protein of interest, mention may be made of polynucleotides encoding an enzyme for resistance to a herbicide, for example the polynucleotide encoding the bar enzyme (White et al., NAR 18:1062, 1990) for tolerance to bialaphos, the polynucleotide encoding the EPSPS enzyme (U.S. Pat. No. 5,188,642; WO 97/04103) for tolerance to glyphosate, or else the polynucleotide encoding the HPPD enzyme (WO 96/38567) for tolerance to isoxazoles. Mention may also be made of a polynucleotide encoding an insecticidal toxin, for example a polynucleotide encoding a toxin of bacterium *Bacillus thuringiensis* (for example, see International Patent Application WO 98/40490). Other polynucleotides for resistance to diseases may also be contained in these plants, for example a polynucleotide encoding the oxaylate oxidase enzyme as described in patent application EP 0 531 498 or U.S. Pat. No. 5,866,778, or a polynucleotide encoding another antibacterial and/or antifungal peptide, such as those described in patent applications WO 97/30082, WO 99/24594, WO 99/02717, WO 99/53053 and WO 99/91089. Mention may also be made of polynucleotides encoding agronomic characteristics of the plant, in particular a polynucleotide encoding a delta-6 desaturase enzyme, as described in U.S. Pat. Nos. 5,552,306 and 5,614,313, and patent applications WO 98/46763 and WO 98/46764, or a polynucleotide encoding a serine acetyltransferase (SAT) enzyme, as described in patent applications WO 00/01833 and PCT/FR 99/03179.

The following examples make it possible to illustrate the present invention without, however, limiting the scope thereof.

EXAMPLE 1

Identification of the Gene Encoding the *Arabidopsis Thaliana* Arogenate Dehydrogense Enzyme A comparison of the sequences of all the prephenate dehydrogenase and arogenate dehydrogenase enzymes currently available in the public databases revealed four short portions of homologous sequences. The enzymes compared are yeast prephenate dehydrogenase (accession number: Z36065), *Bacillus subtilis* prephenate dehydrogenase (accession number: M80245) and *Synechocystis* prephenate dehydrogenase (accession number: D90910). These portions of homology made it possible to identify an *A. thaliana* gene (accession number: AF096371) initially noted as encoding an enzyme "similar to the specific D-isomer 2-hydroxy acid dehydrogenase". This gene consists of two exons separated by a 94 bp intron. The first exon comprises a 1.08 kb open reading frame containing a putative chloroplast transit peptide sequence located downstream of the first ATG codon. The second exon potentially encodes an 892 bp open reading frame. A very strong homology of approximately 60% exists between the protein sequences deduced from the two exons. This homology extends to 70% if the putative chloroplast transit peptide sequence located in the first exon is not taken into account. In addition, each one of the two predicted protein sequences has the size and possesses the four homologous portions characteristic of the prephenate/arogenate dehydrogenase enzymes. This gene was named TyrA (SEQ ID NO: 1).

EXAMPLE 2

Transcriptional Characterization of TyrA

The size of the transcript of the TyrA gene was determined using the Northern blotting and PCR techniques. Purified mRNAs extracted from young leaves of *A. thialiana* were hybridized with $^{32}$P-radiolabeled probes corresponding to fragments of DNA of the two exons of TyrA. This analysis made it possible to identify a 1.8-1.9 kb transcript very close to the presumed size of an mRNA containing the two exons. In addition, although the complete cDNA could not be amplified by PCR, a 1.5 kb PCR fragment was obtained. This fragment comprises the 5' oligonucleotide (P8 =5'-GCTAAAACTCTTCTCCTTCAATACTTACCTG-3': SEQ ID NO: 30) beginning at position 513 bp, and the 3'oligonucleotide (P7 =5'-CAGTATAATTAGTA-GTCAAGGATC-CTGACTGAGAG-3'; SEQ ID NO: 29) complementary to the 3'UTR and beginning at position 2053 bp. This fragment contains a portion of the first coding sequence (TyrA-A T1) and the complete sequence of the second coding sequence (TyrA-AT2). Analysis of the sequence of this cDNA confirmed the splicing of the intron. The results of the analyses by Northern blotting and PCR strongly suggests the existence of an mRNA transcript containing the two coding regions TyrA -A T1 (SEQ ID NO: 4) and TyrA-AT2 (SEQ ID NO: 6).

EXAMPLE 3

Preparation of Constructs Containing the Various Coding Sequences of the *A. Thaliana* Arogenate Dehydrogenase The first exon TyrA-AT1 was obtained by PCR amplification of the genomic DNA of *A. thaliana* with the oligonucleotide P1 (5'-TCTCCATATGATCTTTCAATCTCAT-TCTCATC-3'; SEQ ID NO: 32) which introduces an Nde I restriction site (underlined) at the first ATG codon, and the oligonucleotide P2 (5'-CTAACTAACTAACTACATACCT-CATCATATCC-3': SEQ ID NO: 24) which is complementary to the 3' end of the first exon and to the 5' end of the intron and introduces a stop codon (underlined). Three constructs lacking the sequence encoding the transit peptide were also produced with the oligonucleotide P3 (5'-CCTCTCTTTCCATATGCTCC-CTTCTC-3'SEQ ID NO: 25) which introduces an Nde I restriction site (underlined) at the second ATG codon (M43) at position 127, the oligonucleotide P4 (5'-CCGCCAGCCACCT-CCATATGAC-CGACACCATCC-3'; SEQ ID NO: 26) which introduces an ATG initiating codon and an Nde I restriction site (underlined) at position 174 from the first ATG codon (V58M), and the oligonucleotide P5 (5'-CGCCACCCCTCATATGCG-TATCGCC-3'; SEQ ID NO: 27) which introduces an ATG initiating codon and an Nde I restriction site (underlined) at position 222 from the first ATG codon (L75M). All the OCR fragments corresponding to the first exon, which may or may not encode a transit peptide, were cloned into the plasmid pPCR-Script (Stratagene). Nde I-BamH I DNA fragments containing the coding sequences, with or without the transit peptide sequence, were then cloned into the plasmid pET21 a(+) (Novagen), leading to the development of the plasmids pET21-TyrA-AT1, with and without transit peptide sequence (pET21-TyrA-AT1-M1,pET21-TyrA-AT1-M43, pET21-TyrA-AT1-M58 and pET21-TyrA-ATi-M75).

Two other oligonucleotides were used to amplify the second coding sequence (TyrA-AT2). The oligonucleotide P6 (5'-GATGCATCTTTGCATATGATGAGGTCA-GAAGATG-3'; SEQ ID NO: 28) introduces an Nde I restriction site (underlined) at the ATG codon of the second open reading frame (at position 1081 from the first ATG codon), and the oligo-nucleotide P7 (5'-CAGTATAATTAG-TAGTCAAGGATCCTGACTGAGAG-3'; SEQ ID NO: 29), complementary to the start of the 3'-UTR, introduces a BamH I restriction site (underlined). The PCR fragment corresponding to the second coding sequence was digested with Nde I-BamH I and then cloned into the plasmid pET21 a(+), giving the plasmid pET21-TyrA-AT2.

The complete coding sequence was reconstituted by assembly of the missing 5'end of the first exon with a partial TyrA-AT cDNA (1.5 kb), obtained by PCR amplification of the *Arabidopsis* cDNA with the oligo-nucleotide P8 (5'-GCTAAAACTCTTCTCCTTCAATACTTACCTG-3'; SEQ ID NO: 30) beginning at position 513 bp from the first ATG codon, and the 3'oligonucleotide P7. An EcoRV restriction site located at position 812 bp from the first ATG codon and present in the 5' end of the partial TyrA-ATc DNA was used for the reconstitution. The partial TyrA-AT cDNA was cloned into the plasmid pPCR-Script. An EcoRV-EcoRV fragment was obtained from the plasmid pPCR-Script-TyrA-AT and then cloned into the plasmid pPCR-Script-TyrA-AT1 digested beforehand with EcoRV. This manipulation led to the plasmid pPCR-Script-TyrA-ATc being obtained. An Ndel-BamHl fragment containing the complete coding sequence was excised from the plasmid pPCR-Script-TyrA-ATc, and then cloned into a plasmid pET21a(+) (Novagen), digested beforehand with Nde 1 and BamH 1, producing the plasmid pET21a(+)-TyrA-ATc. Then, in the same way as for the first exon, four plasmids pET21a(+)-TyrA-ATc were obtained; a plasmid containing the complete coding sequence with the sequence encoding the putative transit peptide, and three plasmids lacking this transit peptide sequence, which was cleaved at three different sites (M43, V58 and L75, see above).

For all the constructs described above, the cDNA inserts were sequenced in order to be sure that no unwanted mutation had been introduced during the PCR amplification.

EXAMPLE 4

Measurement of the Enzyme Activities

The arogenate dehydrogenase activity is measured at 25° C. by spectrophotometric monitoring, at 340 nm, of the formation of NADH or NADPH in a solution containing 50 mM of Tris-HCl, pH 8.6, 300 μm of arogenate and 1 mM of NAD or NADPH in a total volume of 200 μl.

The prephenate dehydrogenase activity is measured at 25° C. by spectrophotometric monitoring, at 340 nm, of the formation of NADH or NADPH in a solution containing 50 mM of Tris-HC1, pH 8.6, 300 μM of prephenate and 1 mM of NAD or NADPH in a total volume of 200 μl.

EXAMPLE 5

Production of Recombinant Arogenate Dehydrogenase

*Eshcerichia coli* AT2471 cells were transformed with each one of the plasmids pET21-TyrA-AT obtained in example 3, and then cultured at 37° C. in 2 liters of Luria-Bertani medium supplemented with 100 μg/ml of carbenicillin. When the culture had reached the equivalent of an absorbance at 600 nm (A600) of 0.6, 1 mM of isopropyl-β-D-thiogalactoside was added to the culture medium in order to induce recombinant protein synthesis. The cells were then cultured for 16 h at 28° C., harvested, and then centrifuged for 20 min at 40 000 g. The pellet was then resuspended in a 50 mM Tris-HC1 buffer, pH 7.5, containing 1 mM EDTA, 1 mM dithiothreitol, 1 mM benzamidine HCl and 5 mM aminocaproic acid, and then sonicated (100 pulses every 3 seconds at power 5) with a Vibra-Cell disrupter (Sonics and Materials, Danbury, Conn., USA). The crude extracts thus obtained were then centrifuged for 20 min at 40 000 g, and the supernatants were used directly for the enzyme assays.

The SDS-PAGE analyses of total protein extracts of the *E. coli* strain AT 2471 containing the various constructs pET21-TyrA-Atc, pET21-TyrA-AT1 and pET21-TyrA-AT2 revealed the presence of three recombinant proteins having molecular masses of 66-68 kDa, 35 kDa and 33-34 kDa, respectively. These molecular masses correspond well to the masses deduced from their respective coding sequences (68786 Da for TyrA-ATc, 34966 Da for Tyr-A-AT1, and 34069 Da for Tyr-A-AT2). For the transformants containing the complete coding sequence (TyrA-Atc) and the first coding sequence (TyrA-AT1), recombinant proteins were observed only with the constructs encoding the proteins M58-TyrA-Atc and M58-TyrA-AT1. The three recombinant proteins were mainly found in the protein bodies. However, the presence of small amounts of recombinant proteins in the soluble protein extracts of *E. coli* made it possible to characterize the biochemical properties.

EXAMPLE 6

Figure 2:
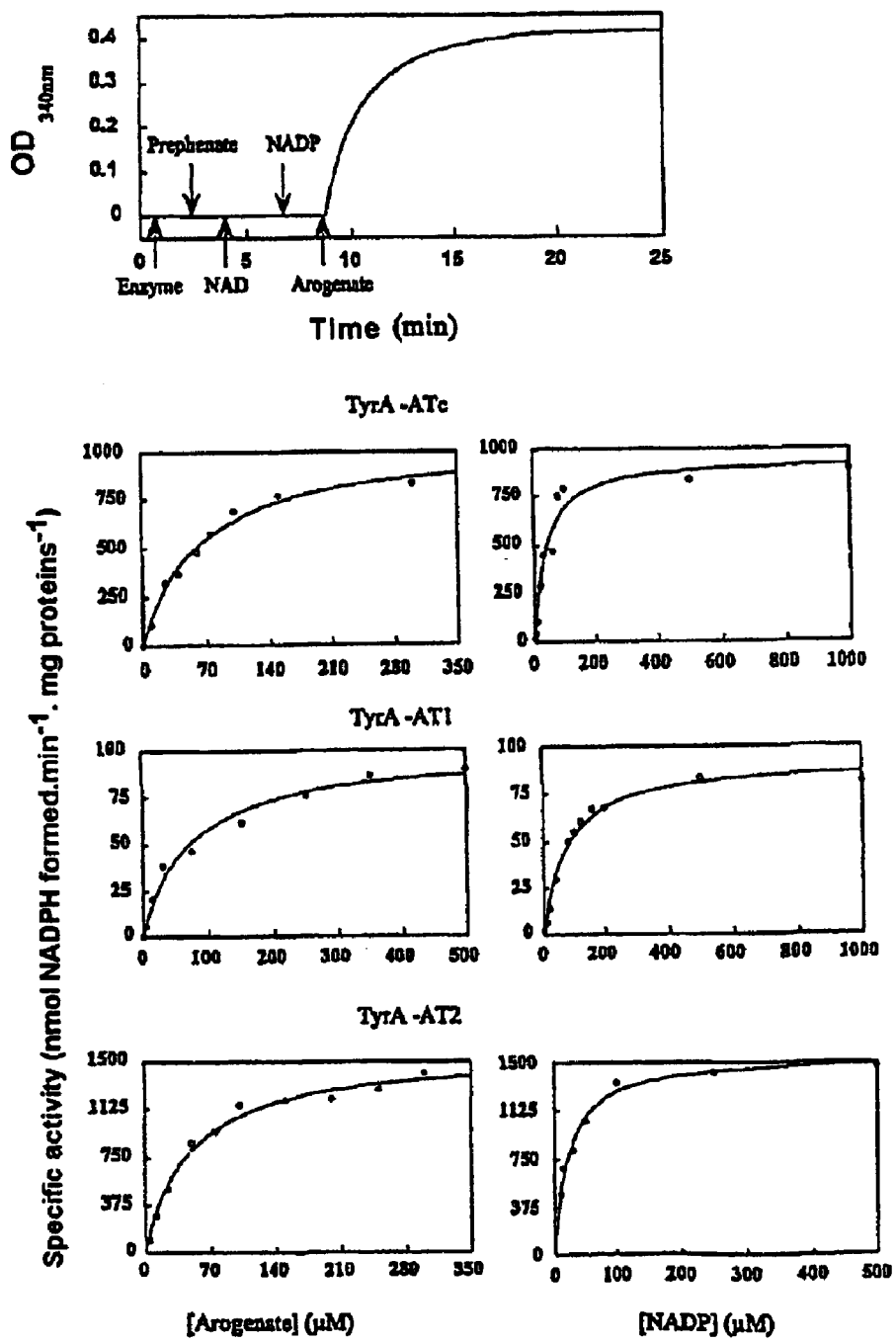
FIG. 2 shows graphs of the enzymatic activity of TyrA-ATc, TyrA-AT1 and TyrA-AT2.

Identification and Biochemical Characterization of the *Arabidopsis Thaliana* Arogenate Dehydrogenase Enzymes The biochemical characterization of the recombinant arogenate dehydrogenase enzymes was carried out using the soluble protein extracts of the transformed *E. coli* strains. The arogenate dehydrogenase activity was measured according to the method described in example 4. A strictly NADP-dependent arogenate dehydrogenase activity was demonstrated for each one of the three recombinant enzymes. No arogenate dehydrogenase activity was detected in the presence of NAD, and no prephenate dehydrogenase activity was detected whatever the cofactor used (NADP or NAD) and whatever the protein tested (TyrA-ATc, TyrA-AT1 or TyrA-AT2). In addition, prephenate at a concentration of 1 mM does not inhibit the arogenate dehydrogenase activity of the three recombinant enzymes. Each one of these enzymes has a Michaelis-Menten-type behavior, and their Km value for arogenate and NADP is relatively the same (FIGS. 2 and 3). The Michaelis constants for NADP are, respectively, 40 µM for TyrA-Atc, 60 µM for TyrA-AT1, and 20 µM for TyrA-AT2. The Michaelis constants for arogenate are, respectively, 70 µM for TyrA-Atc, 45 µM for TyrA-AT1, and 45 µM for TyrA-AT2. In addition, like the other plant arogenate dehydrogenases (Byng et al., 1981, Phytochemistry 6, 1289-1292; Connelly and Conn, 1986, Z. Naturforsch 41c, 69-78; Gaines et al., 1982 Planta 156, 233-240), the Arabidopsis arogenate dehydrogenases are all very sensitive to tyrosine, the product of the enzyme reaction, and insensitive to 1 mM of phenylalanine and 1 mM of p-hydroxyphenylpyruvate. The inhibition by tyrosine is competitive with respect to arogenate (Ki of 14 µM for TyrA-Atc, 8 µM for TyrA-AT1, and 12 µM for TyrA-AT2), and noncompetitive with respect to NADP.

EXAMPLE 7

Identification and Biochemical Characterization of the Syfnechocystis Arogenate Dehydrogenase Enzyme The sequence of the gene encoding the *A. thaliana* arogenate dehyrogenase identified in example 1 (TyrA) made it possible to identify an arogenate dehydrogenase gene in the bacterium *Synechocystis* (accession number: 1652956). This gene was originally described as encoding a "prephenate dehydrogenase" enzyme. It was isolated from a *Synechocystis* genomic library and the enzyme was produced in the same way as the *A. thaliana* enzyme, according to the protocol described in example 5. Biochemical characterization of the enzyme produced made it possible to demonstrate that it is an arogenate dehydrogenase enzyme and not a prephenate dehydrogenase enzyme. This biochemical characterization of the *Synechocystis* arogenate dehydrogenase enzyme was carried out using the purified soluble protein extracts of the transformed *E. coli* strains. The arogenate dehydrogenase activity was measured according to the method described in example 4. A strictly NADP-dependent arogenate dehydrogenase activity was demonstrated for this enzyme. No arogenate dehydrogenase activity was detected in the presence of NAD, and no prephenate dehydrogenase activity was detected whatever the cofactor used (NADP or NAD). In addition, prephenate at a concentration of 1 mM does not inhibit the arogenate dehydrogenase activity of this enzyme. The *Synechocystis* arogenate dehydrogenase has a Michaelis-Menten-type behavior (FIG. 4). The Michaelis constant is 6 µM for NADP, and 107 µM for arogenate.

EXAMPLE 8

Identification of Other Plant Arogenate Dehydrogenase Enzymes

The sequence of the gene encoding the *A. thaliana* arogenate dehydrogenase identified in example 1 (TyrA) made it possible to identify another arogenate dehydrogenase gene in *A. thaliana*. This new gene (accession number: AC0342561; SEQ ID NO: 8) was initially noted as "containing similarity with the embryo abundance protein (EMB20) of *Picea glauca*". It also has a putative chloroplast transit peptide sequence, but no repeat region.

The sequence of the TyrA gene also made it possible to identify two other cDNAs encoding arogenate dehydrogenase enzymes in the public EST (Expressed Sequence Tags) databases. One of these cDNAs, which is not complete, corresponds to a tomato cDNA (TC41067; SEQ ID NO: 22). The incomplete nature of this cDNA does not make it possible to determine whether it is duplicated like TyrA, since its 3' end stops just after the codon corresponding to D356 of Tyr-AT1. The second cDNA corresponds to a complete cDNA of *Picea glauca* (accession number: L47749; SEQ ID NO: 10) and does not possess a repeat region. This *Picea glauca* cDNA was noted as being an "embryo abundance protein".

The invention claimed is:

1. A method for identifying a herbicidal compound having as a target an enzyme with arogenate dehydrogenase activity, said method comprising the steps of
   (a) preparing at least two samples, each containing an equivalent amount of an arogenate dehydrogenase enzyme in solution;
   (b) treating one of the samples with a compound;
   (c) measuring the arogenate dehydrogenase activity in each one of said samples;
   (d) comparing the activity of the treated sample with the activity of the untreated sample or samples, wherein the compound used in step (b) is identified as being a herbicidal compound when the activity measured in step (c) is significantly less in the treated sample compared to the untreated sample or samples; and
   (e) treating plants with the compound identified in step (d) to validate the herbicidal activity of said compound.

2. The method as claimed in claim 1, wherein the arogenate dehydrogenase enzyme in step (a) is is encoded by SEQ ID NO: 1, SEQ ID NO: 2, SEQ ID NO: 4, SEQ ID NO: 6 or SEQ ID NO: 8.

* * * * *